United States Patent
Denison et al.

(10) Patent No.: US 9,397,211 B2
(45) Date of Patent: Jul. 19, 2016

(54) LATERAL MOSFET WITH BURIED DRAIN EXTENSION LAYER

(71) Applicant: Texas Instruments Incorporated, Dallas, TX (US)

(72) Inventors: Marie Denison, Plano, TX (US); Philip L. Hower, Concord, MA (US); Sameer Pendharkar, Allen, TX (US)

(73) Assignee: TEXAS INSTRUMENTS INCORPORATED, Dallas, TX (US)

( * ) Notice: Subject to any disclaimer, the term of this patent is extended or adjusted under 35 U.S.C. 154(b) by 0 days.

(21) Appl. No.: 14/559,239

(22) Filed: Dec. 3, 2014

(65) Prior Publication Data

US 2015/0179793 A1    Jun. 25, 2015

Related U.S. Application Data

(60) Provisional application No. 61/918,324, filed on Dec. 19, 2013.

(51) Int. Cl.
| | |
|---|---|
| *H01L 29/78* | (2006.01) |
| *H01L 29/06* | (2006.01) |
| *H01L 29/08* | (2006.01) |
| *H01L 29/66* | (2006.01) |
| *H01L 29/10* | (2006.01) |
| *H01L 21/324* | (2006.01) |
| *H01L 21/225* | (2006.01) |
| *H01L 21/761* | (2006.01) |
| *H01L 21/266* | (2006.01) |
| *H01L 29/40* | (2006.01) |
| *H01L 29/423* | (2006.01) |

(52) U.S. Cl.
CPC .......... *H01L 29/7823* (2013.01); *H01L 21/225* (2013.01); *H01L 21/324* (2013.01); *H01L 21/761* (2013.01); *H01L 29/0634* (2013.01); *H01L 29/0692* (2013.01); *H01L 29/0847* (2013.01); *H01L 29/0878* (2013.01); *H01L 29/1095* (2013.01); *H01L 29/66659* (2013.01); *H01L 29/66681* (2013.01); *H01L 29/7835* (2013.01); *H01L 21/2253* (2013.01); *H01L 21/266* (2013.01); *H01L 29/1045* (2013.01); *H01L 29/1083* (2013.01); *H01L 29/402* (2013.01); *H01L 29/42368* (2013.01)

(58) Field of Classification Search
CPC .................................................. H01L 29/7823
See application file for complete search history.

(56) References Cited

U.S. PATENT DOCUMENTS

| | | | |
|---|---|---|---|
| 7,964,485 B1* | 6/2011 | French | H01L 21/2253 438/548 |
| 2010/0025726 A1* | 2/2010 | Paul | H01L 29/0634 257/141 |
| 2010/0032756 A1* | 2/2010 | Pendharkar | H01L 21/761 257/337 |
| 2012/0112277 A1* | 5/2012 | Denison | H01L 21/823814 257/337 |

* cited by examiner

*Primary Examiner* — Matthew Reames
*Assistant Examiner* — Steven B Gauthier
(74) *Attorney, Agent, or Firm* — Daniel Chan; Frank D. Cimino

(57) ABSTRACT

An integrated circuit containing an extended drain MOS transistor which has a drift layer, an upper RESURF layer over and contacting an upper surface of the drift layer, and a buried drain extension below the drift layer which is electrically connected to the drift layer at the drain end and separated from the drift layer at the channel end. A lower RESURF layer may be formed between the drift layer and the buried drain extension at the channel end. Any of the upper RESURF layer, the drift layer, the lower RESURF layer and the buried drain extension may have a graded doping density from the drain end to the channel end. A process of forming an integrated circuit containing an extended drain MOS transistor which has the drift layer, the upper RESURF layer, and the buried drain extension.

9 Claims, 26 Drawing Sheets

LATERAL MOSFET WITH BURIED DRAIN EXTENSION LAYER

CROSS-REFERENCE TO RELATED APPLICATIONS

This application claims the benefit of priority under U.S.C. §119(e) of U.S. Provisional Application 61/918,324, filed Dec. 19, 2013, which is hereby incorporated by reference in its entirety.

FIELD OF THE INVENTION

This invention relates to the field of integrated circuits. More particularly, this invention relates to extended drain MOS transistors in integrated circuits.

BACKGROUND OF THE INVENTION

An extended drain metal oxide semiconductor (MOS) transistor is included in an integrated circuit, for example to modulate current from a voltage node above 100 volts. It is desirable to reduce an area of the extended drain MOS transistor, while maintaining a desired current density and/or operating voltage, and/or to reduce the number of photolithographic operations used to fabricate the integrated circuit.

SUMMARY OF THE INVENTION

The following presents a simplified summary in order to provide a basic understanding of one or more aspects of the invention. This summary is not an extensive overview of the invention, and is neither intended to identify key or critical elements of the invention, nor to delineate the scope thereof. Rather, the primary purpose of the summary is to present some concepts of the invention in a simplified form as a prelude to a more detailed description that is presented later.

An integrated circuit may include an extended drain MOS transistor with a upper RESURF layer above a drift layer, a lower RESURF layer below the drift layer and a buried drain extension below the lower RESURF region, the buried drain extension being connected to the drift layer. Doping distributions in any of the upper RESURF layer, the drift layer, the lower RESURF layer and the buried drain extension may be graded, for example to increase a uniformity of electric fields in the drift layer.

DETAILED DESCRIPTION OF EXAMPLE EMBODIMENTS

Figure 1:
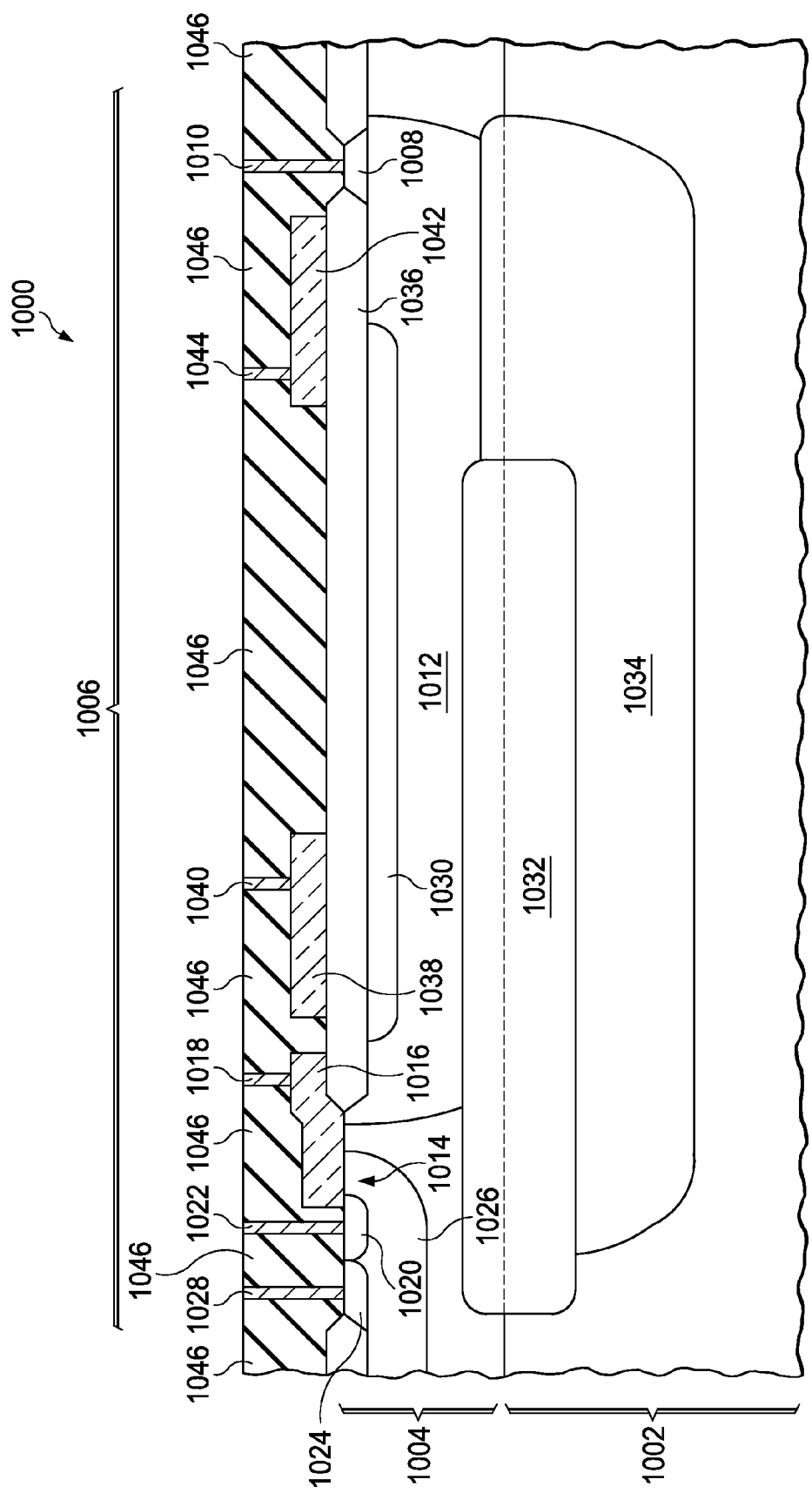
FIG. 1 is a cross-section of an integrated circuit containing an extended drain MOS transistor formed according to an example.

The present invention is described with reference to the attached figures, wherein like reference numerals are used throughout the figures to designate similar or equivalent elements. The figures are not drawn to scale and they are provided merely to illustrate the invention. Several aspects of the invention are described below with reference to example applications for illustration. It should be understood that numerous specific details, relationships, and methods are set forth to provide an understanding of the invention. One skilled in the relevant art, however, will readily recognize that the invention can be practiced without one or more of the specific details or with other methods. In other instances, well-known structures or operations are not shown in detail to avoid obscuring the invention. The present invention is not limited by the illustrated ordering of acts or events, as some acts may occur in different orders and/or concurrently with other acts or events. Furthermore, not all illustrated acts or events are required to implement a methodology in accordance with the present invention.

An extended drain MOS transistor is formed in an integrated circuit. The extended drain MOS transistor has a drift layer between a drain and a channel of the MOS transistor to provide capability to operate above 100 volts. An upper RESURF layer above is formed above the drift layer and a lower RESURF layer is formed below the drift layer. The upper RESURF layer and the lower RESURF layer have an opposite conductivity type from the drift layer. A buried drain extension connected to the drift layer is formed below the lower RESURF region, the buried drain has the same conductivity type as the drift layer. Doping distributions in any combination of the upper RESURF layer, the drift layer, the lower RESURF layer and the buried drain extension may be graded by segmenting ion implant masks used to form the respective layers.

For the purposes of this description, the term "RESURF" will be understood to refer to a material which reduces an electric field in an adjacent semiconductor region. A RESURF region may be for example a semiconductor region with an opposite conductivity type from the adjacent semiconductor region. RESURF structures are described in Appels, et. al., "Thin Layer High Voltage Devices" Philips J, Res. 35 1-13, 1980.

For the purposes of this description, the term "substantially equal" as applied to structures and elements formed in an integrated circuit is understood to mean equal within fabrication tolerances used to fabricate the integrated circuit.

FIG. 1 is a cross-section of an integrated circuit containing an extended drain MOS transistor formed according to an example. The integrated circuit 1000 is disposed in and on a semiconductor substrate 1002, which may be a single crystal silicon wafer, a silicon-on-insulator (SOI) wafer, a hybrid orientation technology (HOT) wafer with regions of different crystal orientations, or other material appropriate for fabrication of the integrated circuit 1000. In versions of the instant example featuring an n-channel MOS transistor, the substrate 1002 is p-type. An epitaxial layer 1004 is disposed on the substrate 1002 with a same conductivity type as the substrate 1002. The extended drain MOS transistor 1006 includes a drain diffused contact region 1008 in the epitaxial layer 1004. The drain diffused contact region 1008 is connected to a drain contact 1010. A drift layer 1012 with the same conductivity type as the drain diffused contact region 1008 is disposed in the epitaxial layer 1004 contacting the drain diffused contact region 1008. A gate contact 1018 is connected to the gate 1016. A source region 1020 of the MOS transistor 1006 in the epitaxial layer 1004 adjacent to the gate 1016 abuts a channel region 1014 under the gate 1016. A source contact 1022 is connected to the source region 1020. The source region 1020 has the same conductivity type as the drain diffused contact region 1008. A body diffused contact region 1024 in the epitaxial layer 1004 of the opposite conductivity type from the drain diffused contact region 1008 is disposed proximate to the source region 1020. The body diffused contact region 1024 contacts a backgate well 1026 of the MOS transistor 1006 which extends under the source region 1020 and under the gate 1016. The backgate well 1026 has the opposite conductivity type from the drain diffused contact region 1008. A body contact 1028 connects to the body diffused contact region 1024.

An upper RESURF layer 1030 is disposed over, and contacting a top surface of, the drift layer 1012 in the epitaxial layer 1004. The upper RESURF layer 1030 is a semiconductor material with an opposite conductivity type from the drift layer 1012. An optional lower RESURF layer 1032 is disposed under, and contacting a bottom surface of, the drift layer 1012. The lower RESURF layer 1032 if formed may be disposed in the epitaxial layer 1004 and/or in the substrate 1002. The lower RESURF layer 1032 is a semiconductor material with an opposite conductivity type from the drift layer 1012. A buried drain extension 1034 of the same conductivity type as the drift layer 1012 is disposed under, and contacting a bottom surface of, the lower RESURF layer 1032 if present. If the lower RESURF layer 1032 is not present, a region of epitaxial layer 1004 exists between the buried drain extension 1034 and the drift layer 1012 proximate to the channel region. The buried drain extension 1034 is electrically connected to the drift layer 1012 proximate to the drain diffused contact region 1008 and separated from the drift layer 1012 proximate to the channel region.

A local average doping density of the drift layer 1012 proximate to the drain diffused contact region 1008 may be between $5\times10^{15}$ cm$^{-3}$ and $5\times10^{16}$ cm$^{-3}$. A doping density in the drift layer 1012 may have be lower proximate to the channel region 1014 compared to proximate to the drain diffused contact region 1008. For example, a local average doping density of the drift layer 1012 proximate to the channel region 1014 may be between 5 and 20 times lower than the local average doping density of the drift layer 1012 proximate to the drain diffused contact region 1008.

A local average doping density of the upper RESURF layer 1030 proximate to the channel region 1014 may be between $1\times10^{16}$ cm$^{-3}$ and $5\times10^{17}$ cm$^{-3}$. A doping density in the upper RESURF layer 1030 may be lower proximate to the drain diffused contact region 1008 compared to proximate to the channel region 1014. For example, a local average doping density of the upper RESURF layer 1030 proximate to the drain diffused contact region 1008 may be between 5 and 20 times lower than the local average doping density of the upper RESURF layer 1030 proximate to the channel region 1014.

A local average doping density of the lower RESURF layer 1032 proximate to the channel region 1014 may be between $1\times10^{15}$ cm$^{-3}$ and $1\times10^{17}$ cm$^{-3}$. A doping density in the lower RESURF layer 1032 may be lower proximate to the drain diffused contact region 1008 compared to proximate to the channel region 1014. For example, a local average doping density of the lower RESURF layer 1032 proximate to the drain diffused contact region 1008 may be between 5 and 20 times lower than the local average doping density of the lower RESURF layer 1032 proximate to the channel region 1014.

A local average doping density of the buried drain extension 1034 proximate to the drain diffused contact region 1008 may be between $5\times10^{15}$ cm$^{-3}$ and $5\times10^{16}$ cm$^{-3}$. A doping density in the buried drain extension 1034 may have be lower proximate to the channel region 1014 compared to proximate to the drain diffused contact region 1008. For example, a local average doping density of the buried drain extension 1034 proximate to the channel region 1014 may be between 5 and 20 times lower than the local average doping density of the buried drain extension 1034 proximate to the drain diffused contact region 1008.

A dielectric layer 1036, for example field oxide, is disposed over the upper RESURF layer 1030. A channel side field plate 1038 is disposed over the dielectric layer 1036 proximate to the gate 1016. An optional channel side field plate contact 1040 may connect to the channel side field plate 1038. A drain side field plate 1042 is disposed over the dielectric layer 1036 proximate to the drain diffused contact region 1008. An optional drain side field plate contact 1044 may connect to the drain side field plate 1042. The drain contact 1010, the gate contact 1018, the source contact 1022, the body contact 1028, optional channel side field plate contact 1040 if present and the optional drain side field plate contact 1044 if present are disposed in a pre-metal dielectric (PMD) layer 1046 disposed over the epitaxial layer 1004.

Figure 2A:
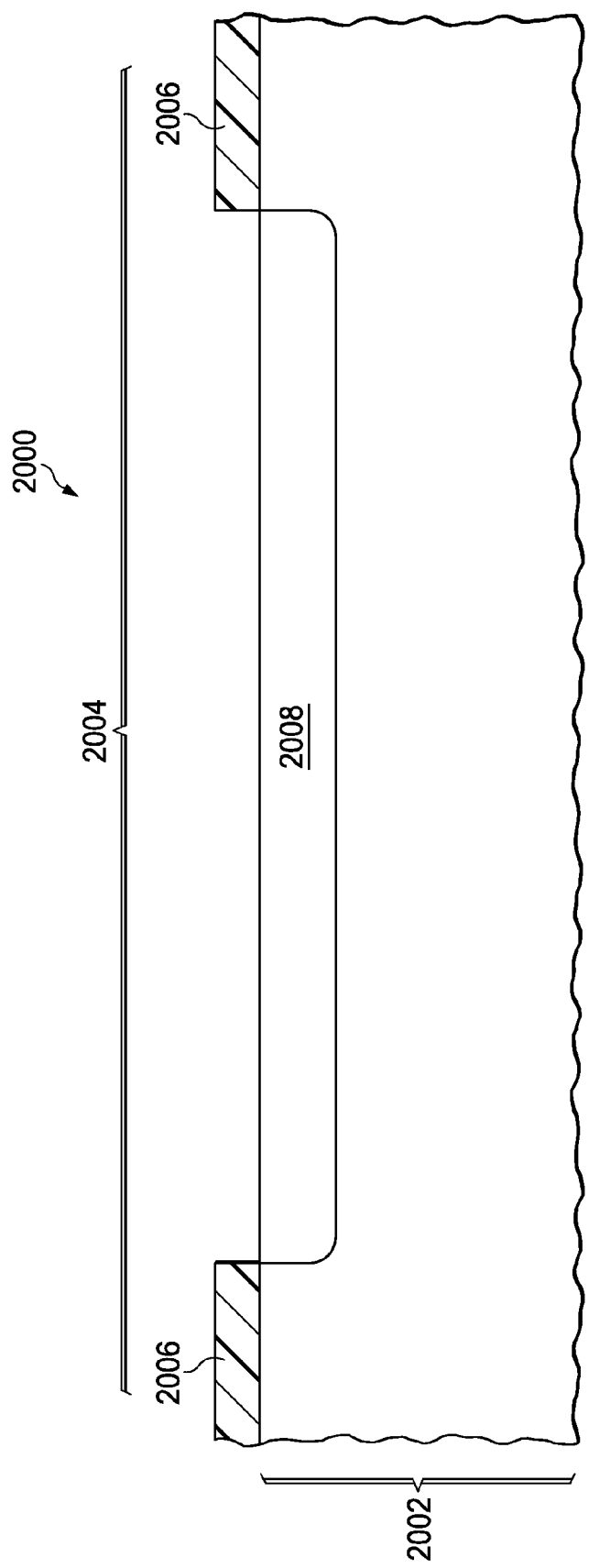
FIG. 2A through FIG. 2F are cross-sections of an integrated circuit containing an extended drain MOS transistor formed according to an example, depicted in successive stages of fabrication.

FIG. 2A through FIG. 2F are cross-sections of an integrated circuit containing an extended drain MOS transistor formed according to an example, depicted in successive stages of fabrication. The instant example will describe formation of an n-channel version of the extended drain MOS transistor. A p-channel extended drain MOS transistor may be formed with appropriate changes of polarities of dopants and conductivity types. Referring to FIG. 2A, the integrated circuit 2000 is formed in and on a p-type substrate 2002 with the properties described in reference to FIG. 1. The integrated circuit 2000 includes an area defined for the extended drain MOS transistor 2004. An optional first layer of sacrificial silicon oxide or other dielectric material, not shown, may be formed on the substrate 2002. A buried drain extension implant mask 2006 is formed over a top surface of the substrate 2002 so as to expose the top surface of the substrate in an area defined for a buried drain extension. The buried drain extension implant mask 2006 may include photoresist and/or inorganic dielectric material such as silicon dioxide or silicon nitride. A buried drain extension ion implant process is performed on the integrated circuit 2000 which implants n-type dopants such as phosphorus, and possibly arsenic and/or antimony, into the substrate 2002 at a dose between $1 \times 10^{11}$ atoms/cm$^2$ and $2 \times 10^{12}$ atoms/cm$^2$ to form a buried drain extension implanted layer 2008 in the area defined for the buried drain extension.

Figure 2B:
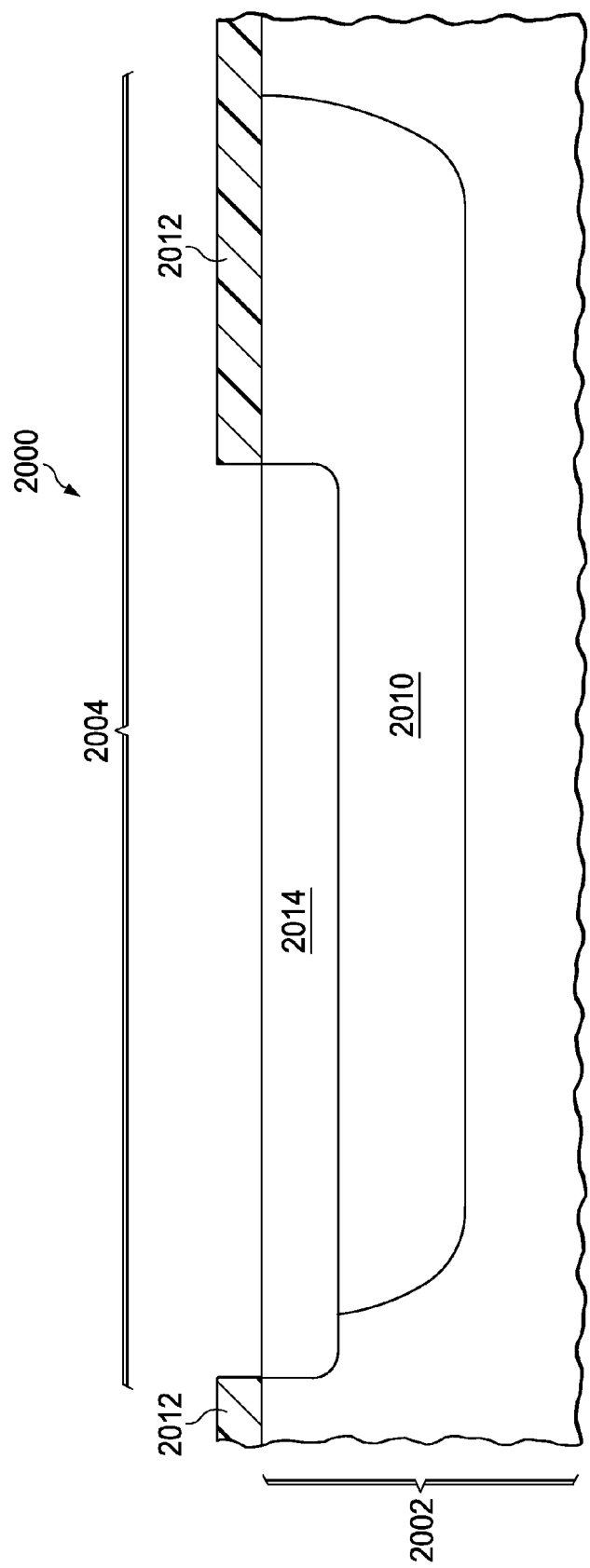

Referring to FIG. 2B, a thermal drive operation is performed on the integrated circuit 2000 which heats the substrate 2002 so that dopants in the buried drain extension implanted layer 2008 of FIG. 2A diffuse outward to form a partially diffused buried drain extension 2010. An optional second layer of sacrificial silicon oxide or other dielectric material, not shown, may be formed on the substrate 2002. A lower RESURF layer implant mask 2012 may be formed over the substrate 2002 so as to expose the top surface of the substrate in an area defined for a lower RESURF layer. The lower RESURF layer implant mask 2012 may include photoresist and/or inorganic dielectric material such as silicon dioxide or silicon nitride. A lower RESURF layer ion implant process may be performed on the integrated circuit 2000 which implants p-type dopants such as boron, gallium and/or indium into the substrate 2002 at a dose between $5 \times 10^{10}$ atoms/cm$^2$ and $1 \times 10^{13}$ atoms/cm$^2$ to form an optional lower RESURF implanted layer 2014 in the area defined for the lower RESURF layer.

Figure 2C:
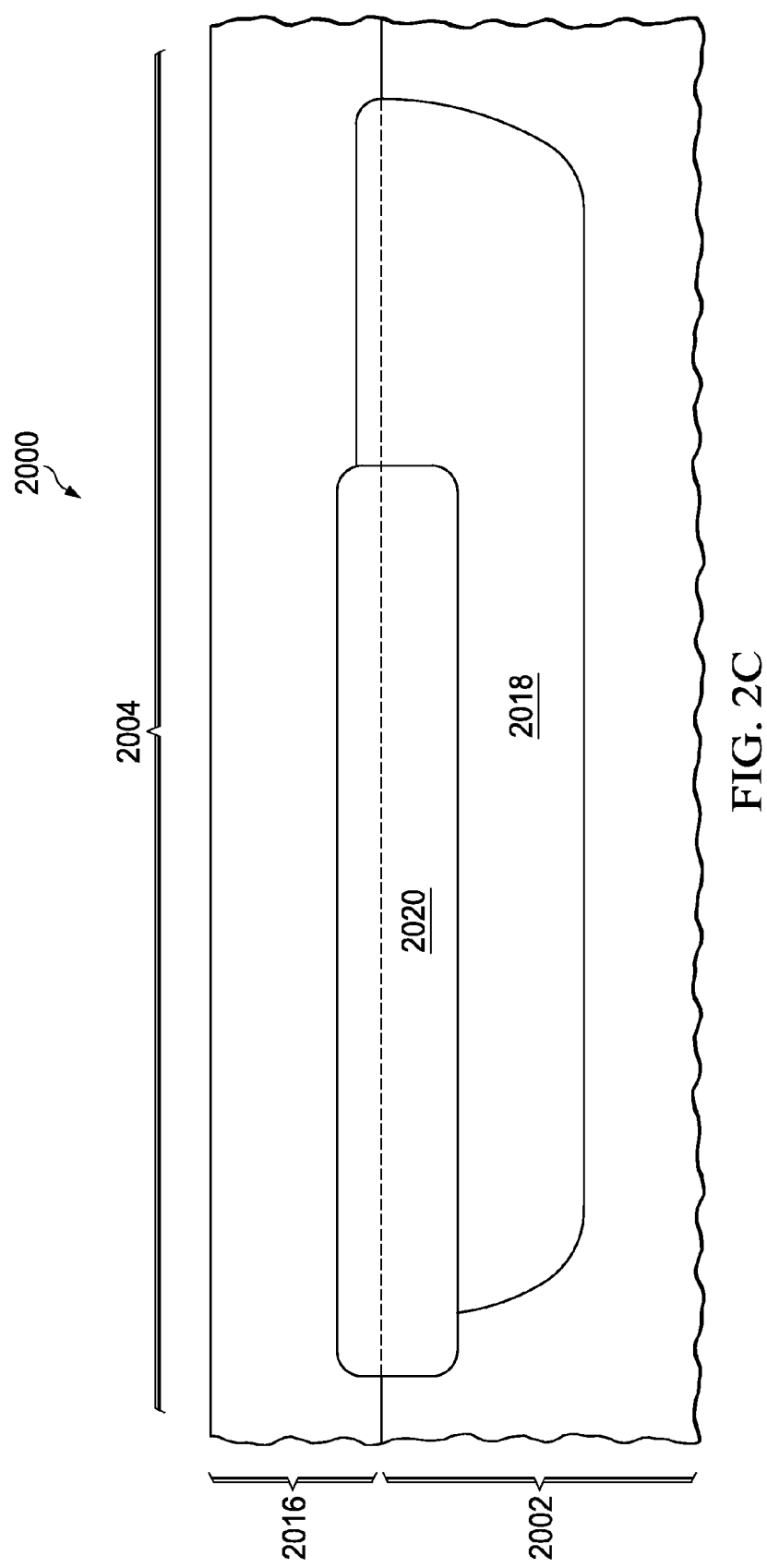

Referring to FIG. 2C, a p-type epitaxial layer 2016 is formed on the top surface of the substrate 2002. Dopants in the partially diffused buried drain extension 2010 and lower RESURF implanted layer 2014 if formed of FIG. 2B diffuse outward to form a buried drain extension 2018 and an optional lower RESURF layer 2020 respectively. A bottom surface of the lower RESURF layer 2020 contacts a top surface of the buried drain extension 2018. In one version of the instant example, the buried drain extension 2018 and the lower RESURF layer 2020 extend into the epitaxial layer 2016 as depicted in FIG. 2C.

Figure 2D:
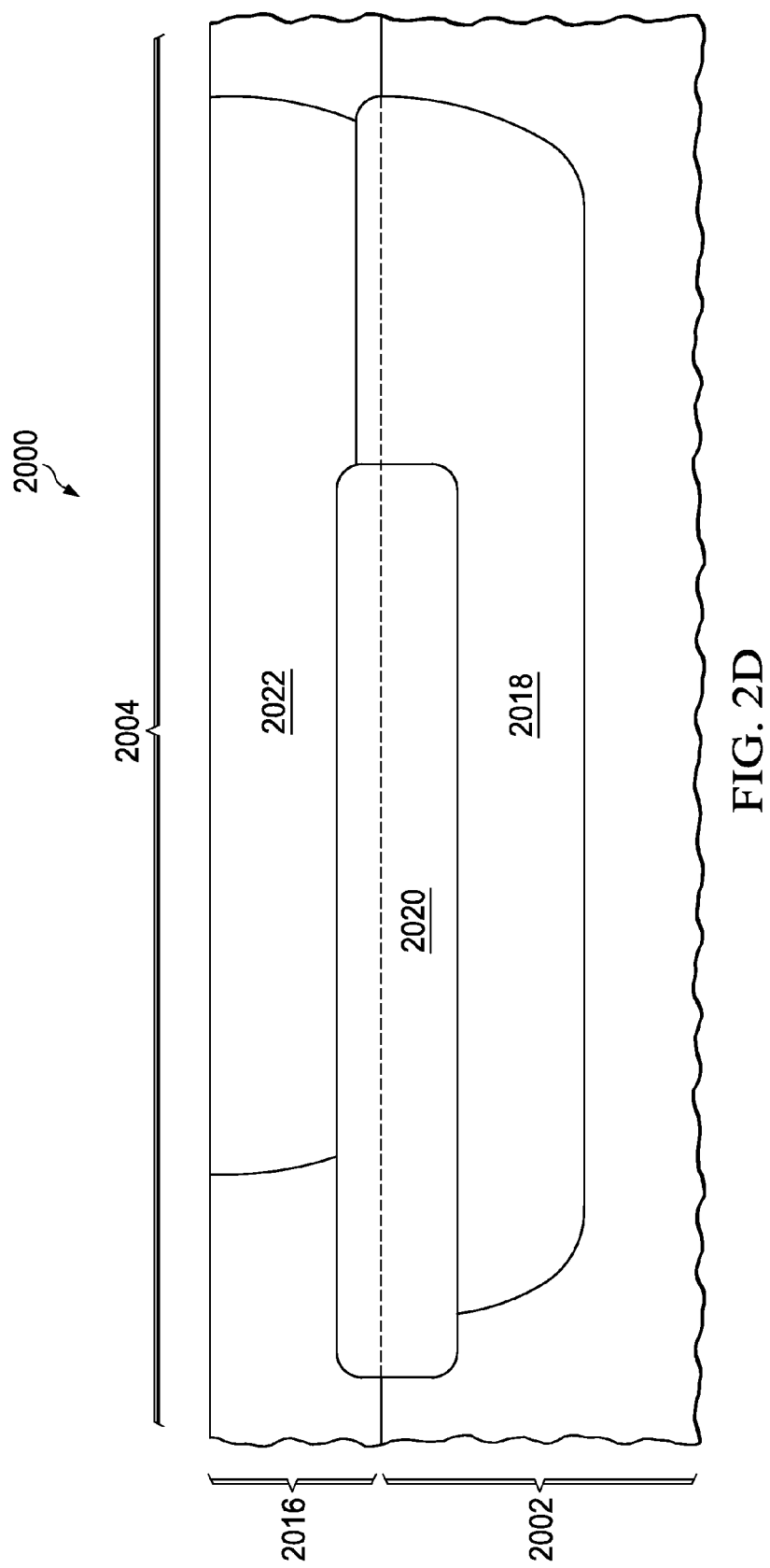

Referring to FIG. 2D, an n-type drift layer 2022 is formed in the epitaxial layer 2016 so that a bottom surface of the drift layer 2022 contacts an upper surface of the lower RESURF layer 2020. The n-type drift layer 2022 may be formed for example by ion implanting n-type dopants such as phosphorus, and possibly arsenic and/or antimony, through an exposed area in a drift layer implant mask, not shown, into the substrate 2002 at a dose between $5 \times 10^{10}$ atoms/cm$^2$ and $1 \times 10^{13}$ atoms/cm$^2$ to form a drift implanted layer, followed by an anneal operation to diffuse the dopants outward. The drift layer 2022 is electrically connected to the buried drain extension 2018 at a drain end and is separated from the buried drain extension 2018 at a channel end. The drift layer 2022 may be formed concurrently with wells used in other components, not shown, of the integrated circuit 2000, for example wells to isolate transistors.

Figure 2E:
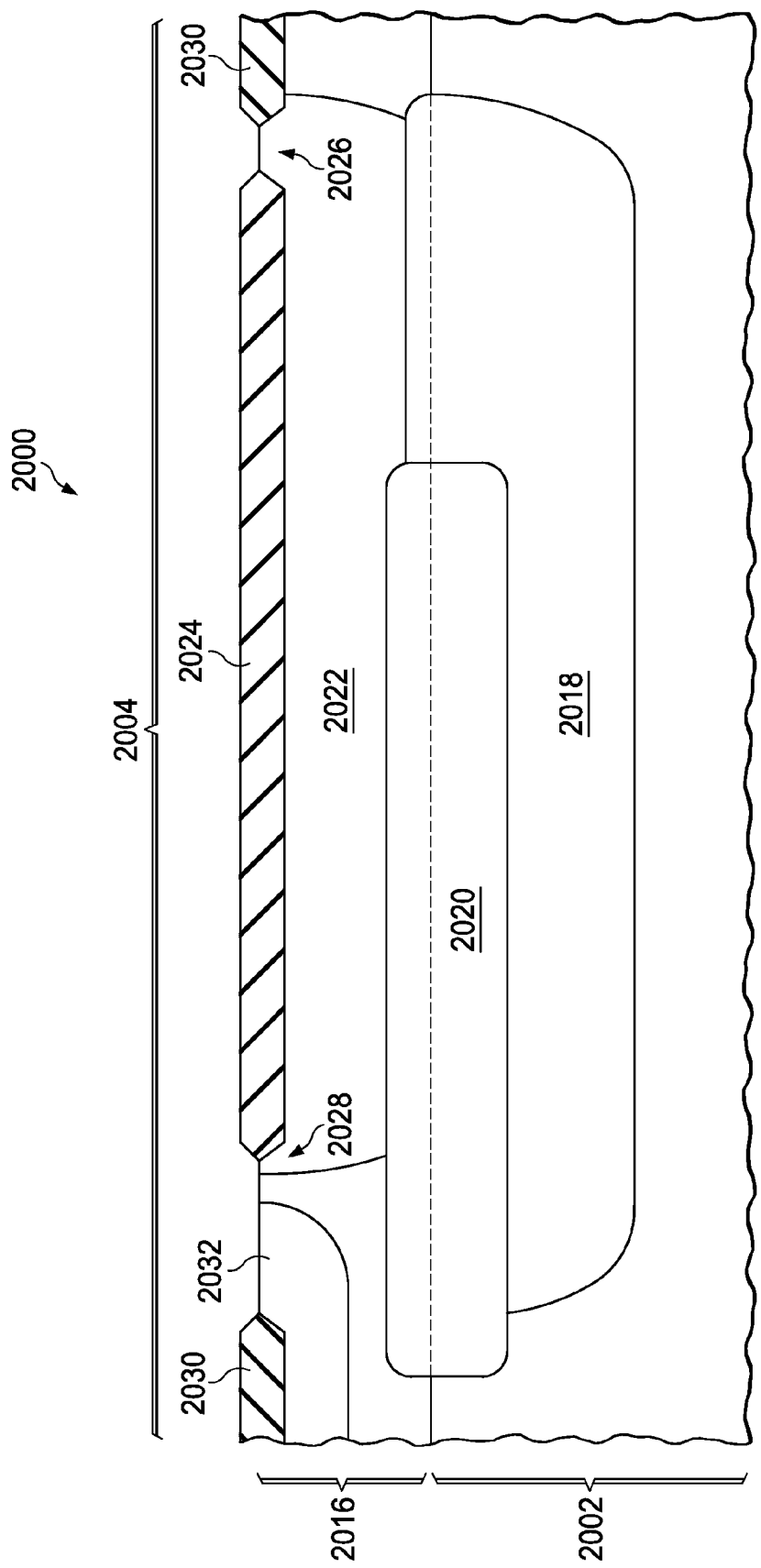

Referring to FIG. 2E, a dielectric layer 2024, for example field oxide, is formed at a top surface of the epitaxial layer 2016 over the drift layer 2022, so as to leave exposed a portion at a drain end 2026 and a portion at a channel end 2028 of the drift layer 2022. Additional dielectric layers 2030 may be formed adjacent to the MOS transistor area 2004, for example to isolate the MOS transistor from other components, not shown, of the integrated circuit 2000. A source well 2032 is formed in the epitaxial layer 2016 adjacent to the channel end 2028 of the drift layer 2022. An average doping density in the source well 2032 may be between $5 \times 10^{16}$ cm$^{-3}$ and $1 \times 10^{16}$ cm$^{-3}$.

Figure 2F:
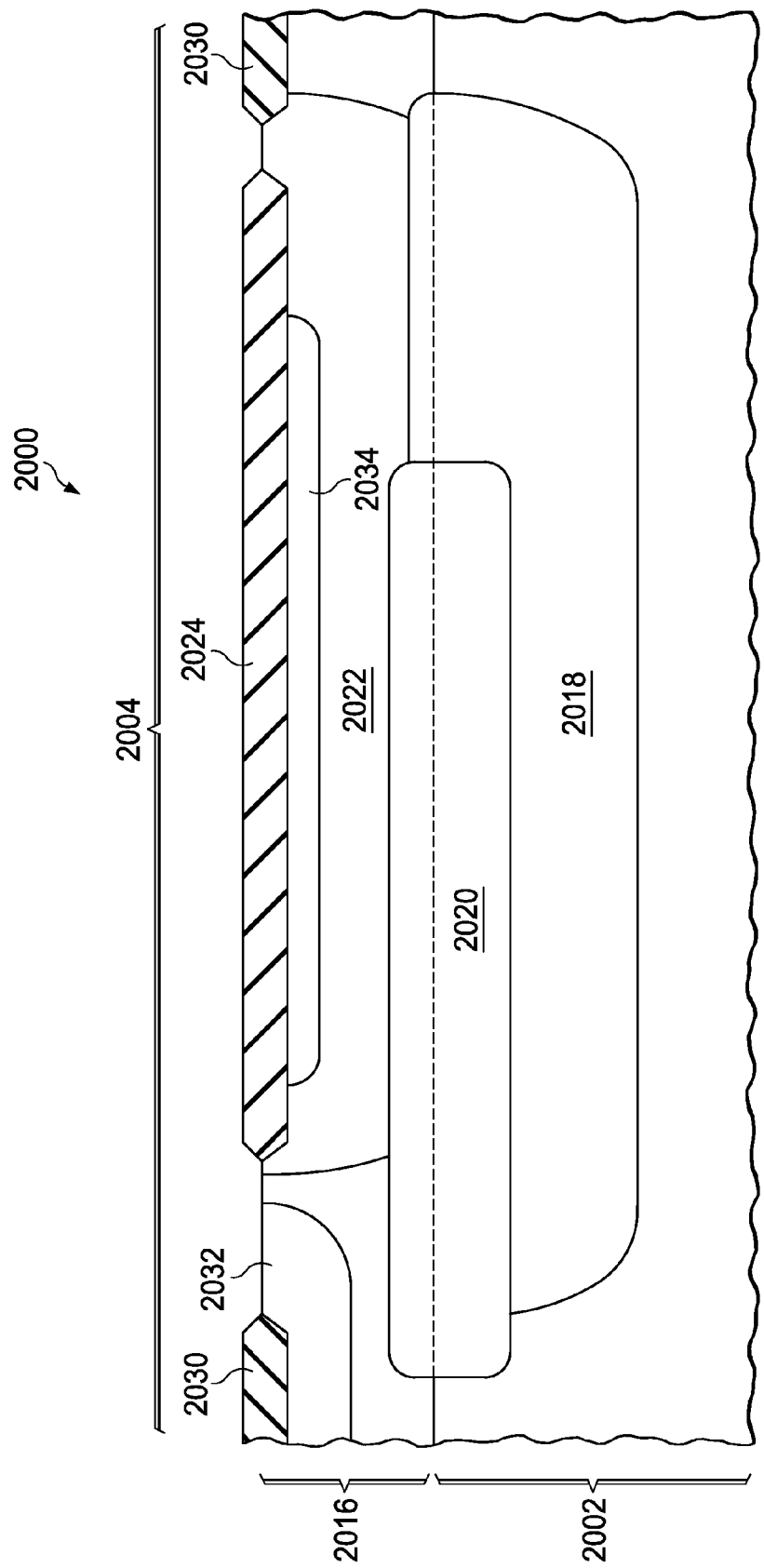

Referring to FIG. 2F, a p-type upper RESURF layer 2034 is formed in the epitaxial layer 2016 so that a bottom surface of the upper RESURF layer 2034 contacts the drift layer 2022. The upper RESURF layer 2034 may be formed for example by ion implanting p-type dopants such as boron, and possibly gallium, through an exposed area in an upper RESURF layer implant mask, not shown, into the epitaxial layer 2016 at a dose between $2 \times 10^{11}$ atoms/cm$^2$ and $1 \times 10^{13}$ atoms/cm$^2$ followed by an anneal operation to diffuse and activate the dopants.

In subsequent operations, a gate, field plates, a drain diffused contact region, a source region, a body diffused contact region, a PMD layer and contacts are formed to provide a structure as described in reference to FIG. 1.

Figure 3A:
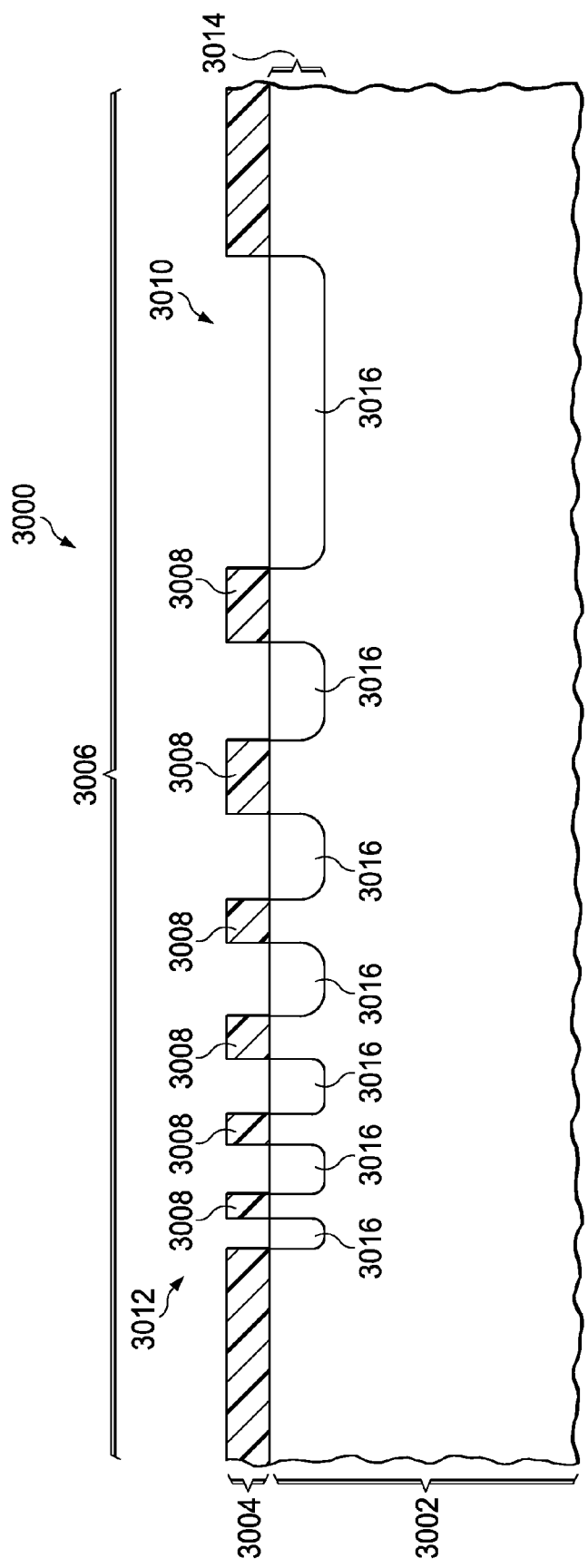
FIG. 3A and FIG. 3B are cross-sections of an integrated circuit including an extended drain MOS transistor with a graded buried drain extension, formed according to an example, depicted in successive stages of fabrication.
Figure 3B:
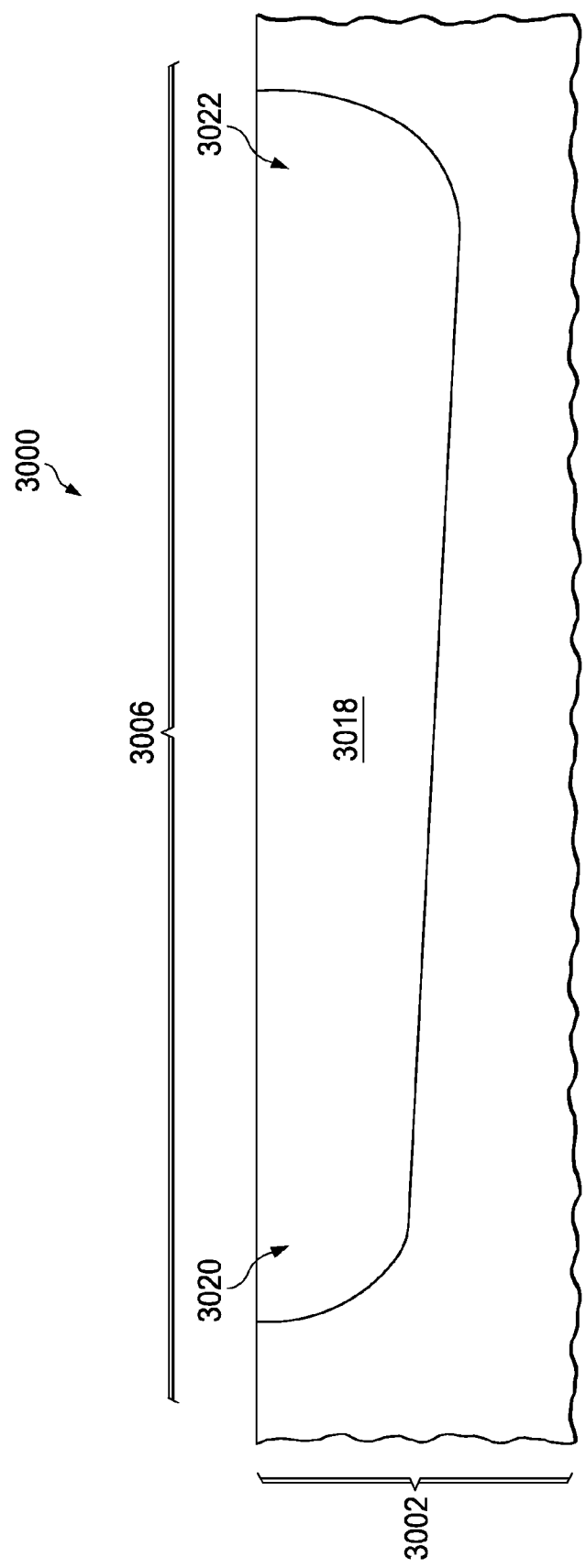

FIG. 3A and FIG. 3B are cross-sections of an integrated circuit including an extended drain MOS transistor with a graded buried drain extension, formed according to an example, depicted in successive stages of fabrication. Referring to FIG. 3A, the integrated circuit 3000 is formed in and on a substrate 3002 with the properties described in reference to FIG. 1. A buried drain extension implant mask 3004 is formed over a top surface of the substrate 3002 so as to expose the top surface of the substrate 3002 in an area defined for a buried drain extension 3006. The buried drain extension implant mask 3004 includes internal blocking elements 3008 with graded widths and/or spaced on graded intervals so that a larger portion of the top surface of the substrate 3002 is exposed in a drain end area 3010 than in a channel end area 3012. The blocking elements 3008 may have substantially equal lateral dimensions or may have substantially different lateral dimensions. The buried drain extension implant mask 3004 may include photoresist and/or inorganic dielectric material such as silicon dioxide or silicon nitride. A buried drain extension ion implant process is performed on the integrated circuit 3000 which implants dopants into the substrate 3002 at a dose between $1 \times 10^{11}$ atoms/cm$^2$ and $2 \times 10^{12}$ atoms/cm$^2$ to form a buried drain extension segmented implanted layer 3014 in the buried drain extension area 3006. The buried drain extension segmented implanted layer 3014 includes implanted segments 3016 which may have different lateral dimensions.

Referring to FIG. 3B, thermal drive operation is performed on the integrated circuit 3000 which heats the substrate 3002 so that dopants in the buried drain extension segmented implanted layer 3014 of FIG. 3A diffuse outward to form a graded partially diffused buried drain extension 3018. Forming the buried drain extension implant mask 3004 with internal blocking elements 3008 as described in reference to FIG. 3A results in the graded partially diffused buried drain extension 3018 having a lower doping density at a channel end 3020 than at a drain end 3022. In one version of the instant example, a local average doping density of a graded buried drain extension in the completed integrated circuit 3000 at the drain end 3022 may be between $5 \times 10^{15}$ cm$^{-3}$ and $5 \times 10^{16}$ cm$^{-3}$, while a local average doping density of the graded buried drain extension at the channel end 3020 may be between 5 and 20 times lower. In one version of the instant example, the graded buried drain extension in the completed integrated circuit 3000 may be electrically discontinuous, that is, the graded buried drain extension may include at least two regions which are separated by semiconductor material of an opposite conductivity type.

Figure 4A:
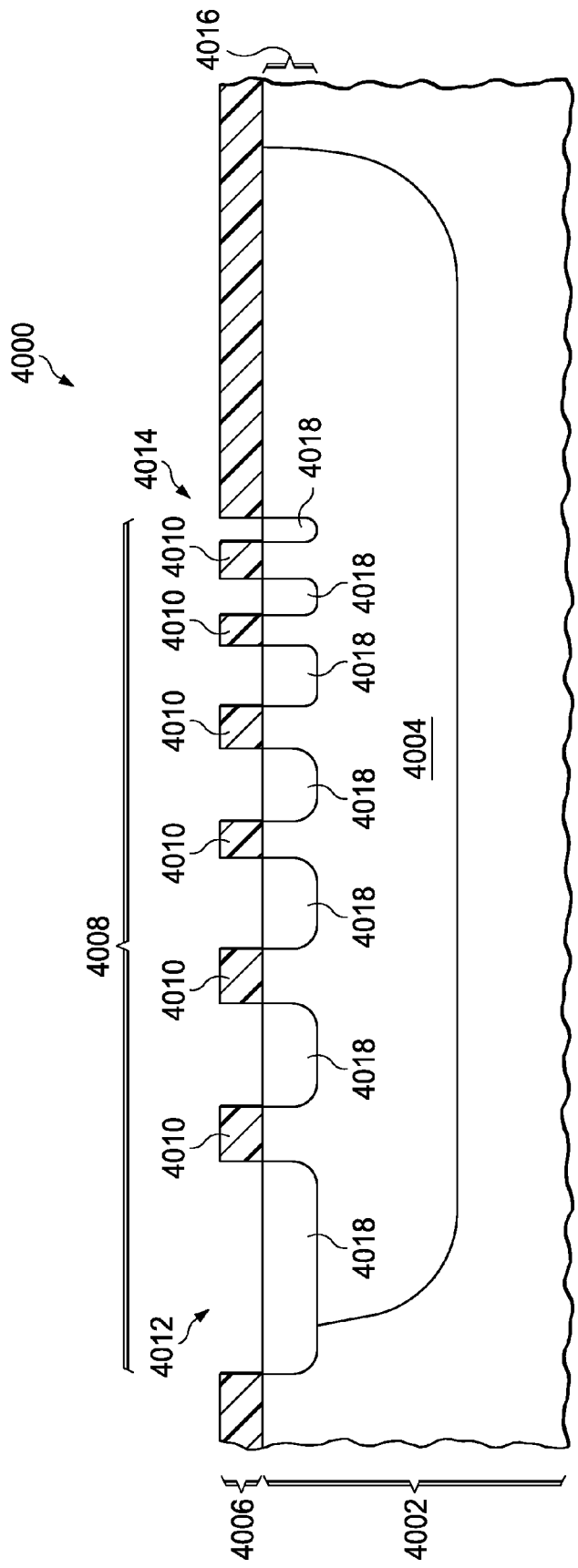
FIG. 4A and FIG. 4B are cross-sections of an integrated circuit including an extended drain MOS transistor with a graded lower RESURF layer, formed according to an example, depicted in successive stages of fabrication.
Figure 4B:
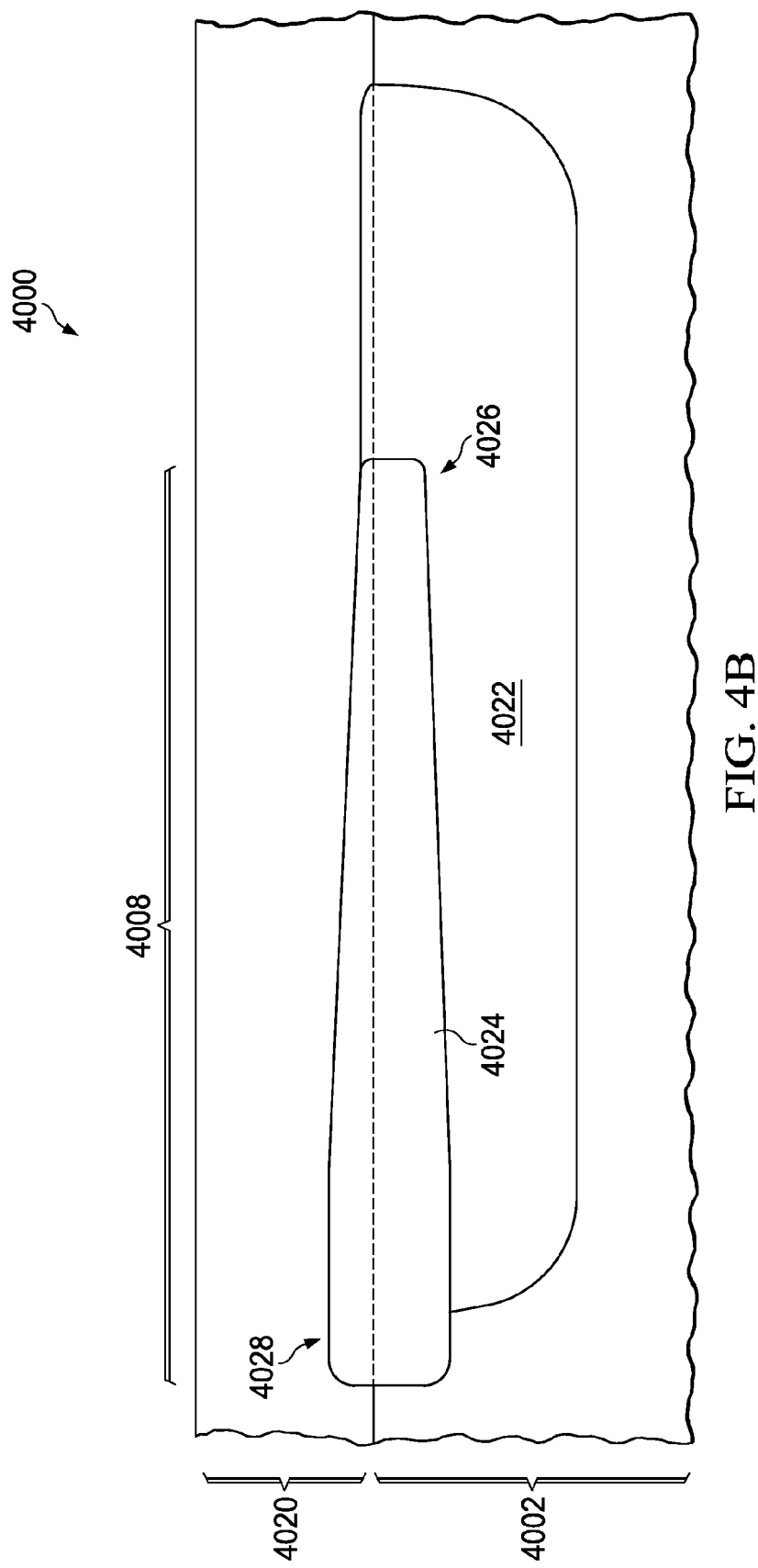

FIG. 4A and FIG. 4B are cross-sections of an integrated circuit including an extended drain MOS transistor with a graded lower RESURF layer, formed according to an example, depicted in successive stages of fabrication. Referring to FIG. 4A, the integrated circuit 4000 is formed in and on a substrate 4002 with the properties described in reference to FIG. 1. A partially diffused buried drain extension 4004 is formed in the substrate 4002 as described in reference to FIG. 2A and FIG. 2B, or possibly as described in reference to FIG. 3A and FIG. 3B. A lower RESURF implant mask 4006 is formed over a top surface of the substrate 4002 so as to expose the top surface of the substrate 4002 in an area defined for a lower RESURF layer 4008. The lower RESURF implant mask 4006 includes internal blocking elements 4010 with graded widths and/or spaced on graded intervals so that a larger portion of the top surface of the substrate 4002 is exposed in a channel end area 4012 than in a drain end area 4014. The blocking elements 4010 may have substantially equal lateral dimensions or may have substantially different lateral dimensions. The lower RESURF implant mask 4006 may include photoresist and/or inorganic dielectric material such as silicon dioxide or silicon nitride. A lower RESURF ion implant process is performed on the integrated circuit 4000 which implants dopants into the substrate 4002 at a dose between $5 \times 10^{10}$ atoms/cm$^2$ and $1 \times 10^{13}$ atoms/cm$^2$ to form a lower RESURF segmented implanted layer 4016 in the lower RESURF layer area 4008. The lower RESURF segmented implanted layer 4016 includes implanted segments 4018 which may have different lateral dimensions.

Referring to FIG. 4B, an epitaxial layer 4020 is formed on the top surface of the substrate 4002 as described in reference to FIG. 2C. Dopants in the partially diffused buried drain extension 4004 and lower RESURF segmented implanted layer 4016 of FIG. 4A diffuse outward to form a buried drain extension 4022 and a graded lower RESURF layer 4024 respectively. A bottom surface of the graded lower RESURF layer 4024 contacts a top surface of the buried drain extension 4022. In one version of the instant example, the buried drain extension 4022 and the graded lower RESURF layer 4024 extend into the epitaxial layer 4020 as depicted in FIG. 4B.

Forming the lower RESURF implant mask 4006 with internal blocking elements 4010 as described in reference to FIG. 4A results in the graded lower RESURF layer 4024 having a lower doping density at a drain end 4026 than at a channel end 4028. In one version of the instant example, a local average doping density of the graded lower RESURF layer 4024 at the channel end 4028 may be between $1 \times 10^{15}$ cm$^{-3}$ and $1 \times 10^{17}$ cm$^{-3}$, while a local average doping density of the graded lower RESURF layer 4024 at the drain end 4026 may be between 5 and 20 times lower. In one version of the instant example, the graded lower RESURF layer 4024 may be electrically discontinuous, that is, the graded lower RESURF layer 4024 may include at least two regions which are separated by semiconductor material of an opposite conductivity type.

Figure 5A:
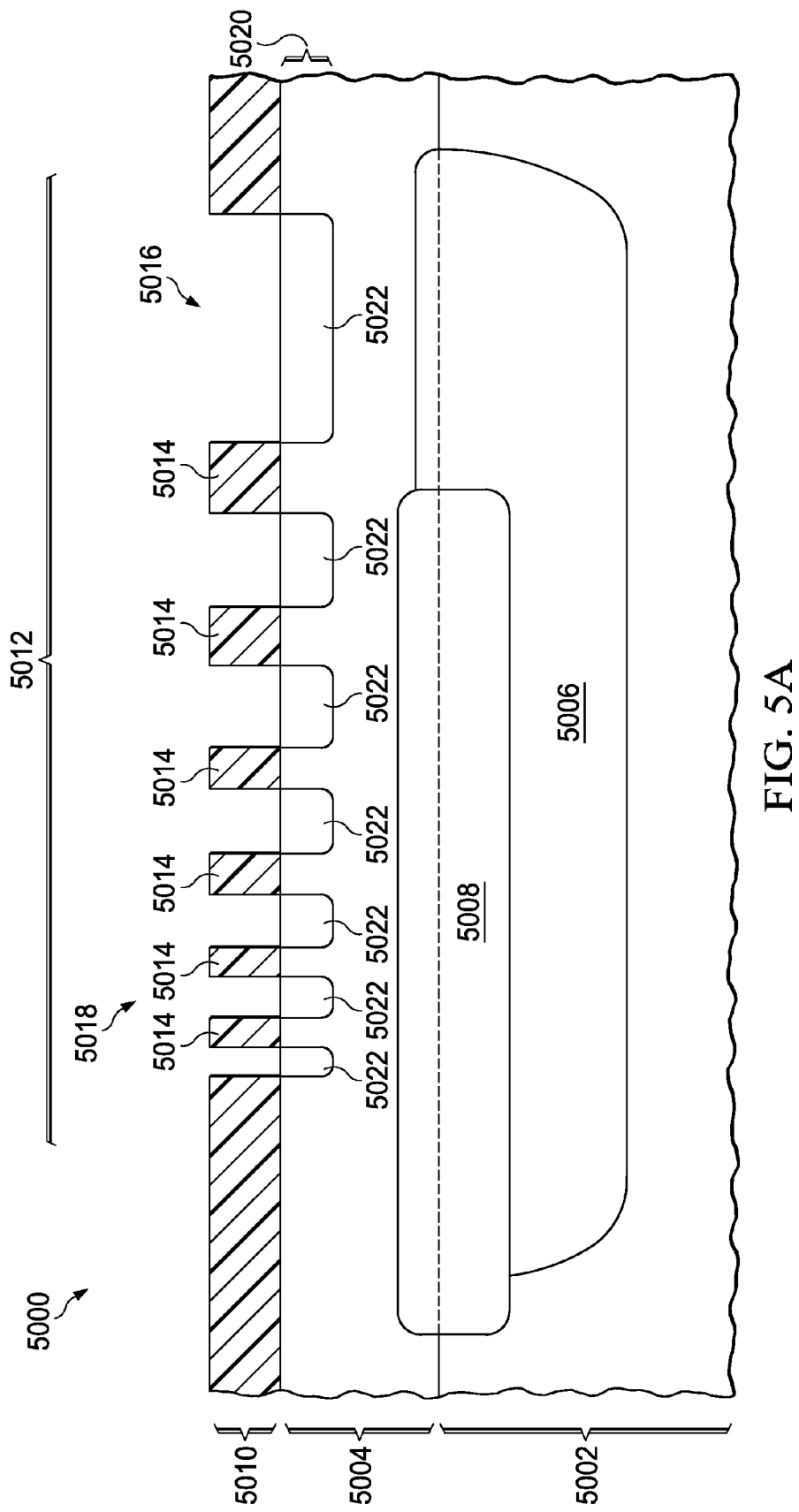
FIG. 5A and FIG. 5B are cross-sections of an integrated circuit including an extended drain MOS transistor with a graded drift layer, formed according to an example, depicted in successive stages of fabrication.
Figure 5B:
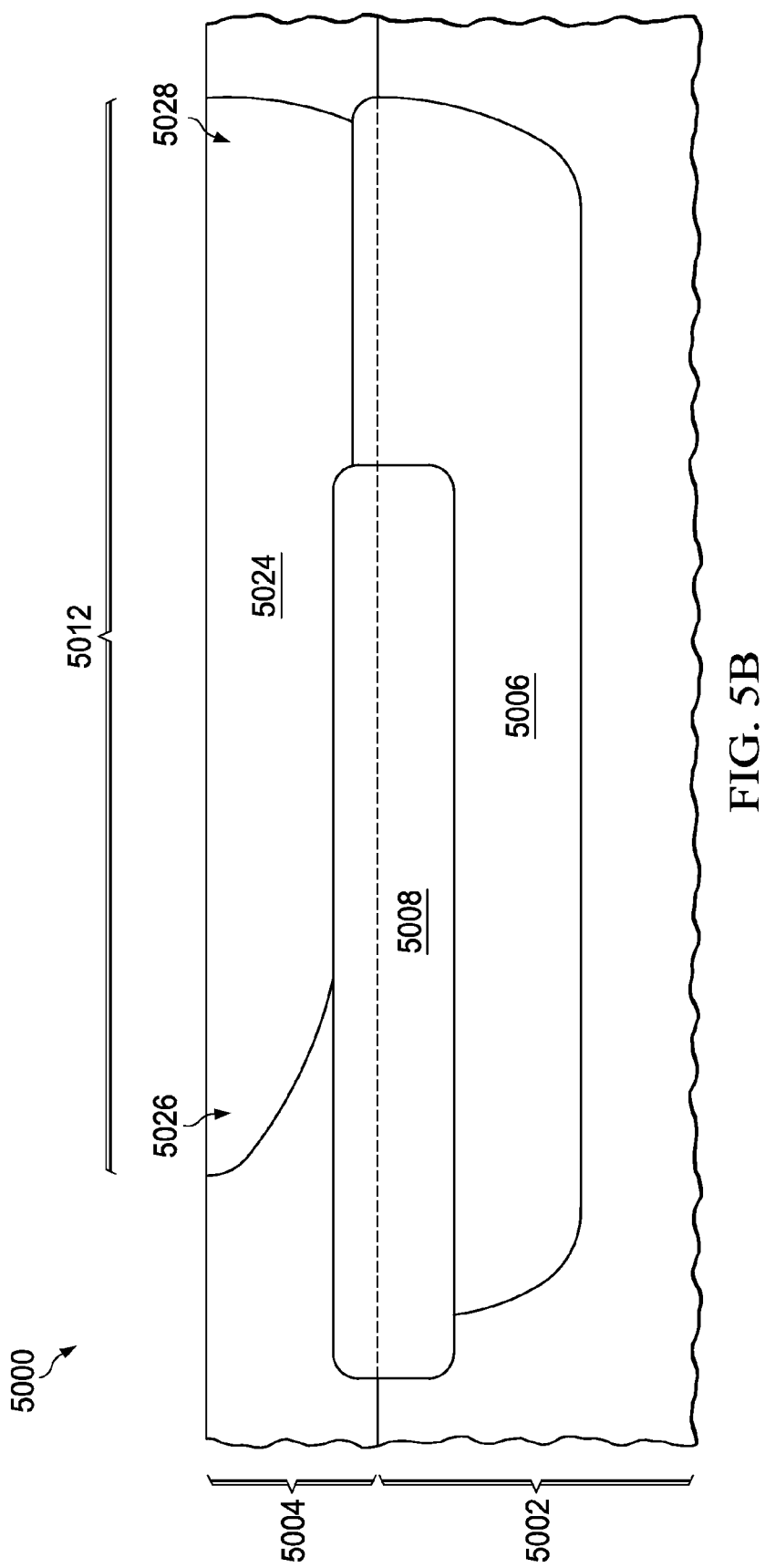

FIG. 5A and FIG. 5B are cross-sections of an integrated circuit including an extended drain MOS transistor with a graded drift layer, formed according to an example, depicted in successive stages of fabrication. Referring to FIG. 5A, the integrated circuit 5000 is formed in and on a substrate 5002 with the properties described in reference to FIG. 1. An epitaxial layer 5004 is formed on a top surface of the substrate 5002 as described in reference to FIG. 2A through FIG. 2C. A buried drain extension 5006 is formed in the substrate 5002 and epitaxial layer 5004 as described in reference to FIG. 2A through FIG. 2C, or possibly as described in reference to FIG. 3A and FIG. 3B. A lower RESURF layer 5008 is formed in the substrate 5002 and epitaxial layer 5004 as described in reference to FIG. 2B and FIG. 2C, or possibly as described in reference to FIG. 4A and FIG. 4B.

A drift layer implant mask 5010 is formed over a top surface of the epitaxial layer 5004 so as to expose the top surface of the epitaxial layer 5004 in an area defined for a drift layer 5012. The drift layer implant mask 5010 includes internal blocking elements 5014 with graded widths and/or spaced on graded intervals so that a larger portion of the top surface of the epitaxial layer 5004 is exposed in a drain end area 5016 than in a channel end area 5018. The blocking elements 5014 may have substantially equal lateral dimensions or may have substantially different lateral dimensions. The drift layer implant mask 5010 may include photoresist and/or inorganic dielectric material such as silicon dioxide or silicon nitride. A drift layer implant process is performed on the integrated circuit 5000 which implants dopants into the epitaxial layer 5004 at a dose between $5 \times 10^{10}$ atoms/cm$^2$ and $1 \times 10^{13}$ atoms/cm$^2$ to form a drift segmented implanted layer 5020 in the epitaxial layer 5004. The drift segmented implanted layer 5020 includes implanted segments 5022 which may have different lateral dimensions.

Referring to FIG. 5B, an anneal operation is performed on the integrated circuit 5000 as described in reference to FIG. 2D. Dopants in the drift segmented implanted layer 5020 of FIG. 5A diffuse outward to form a graded drift layer 5024. A bottom surface of the graded drift layer 5024 contacts a top surface of the lower RESURF layer 5008. Forming the drift layer implant mask 5010 with internal blocking elements 5014 as described in reference to FIG. 5A results in the graded drift layer 5024 having a lower doping density at a channel end 5026 than at a drain end 5028. In one version of the instant example, a local average doping density of the graded drift layer 5024 at the drain end 5028 may be between $5 \times 10^{15}$ cm$^{-3}$ and $5 \times 10^{16}$ cm$^{-3}$, while a local average doping density of the graded drift layer 5024 at the channel end 5026 may be between 5 and 20 times lower.

Figure 6A:
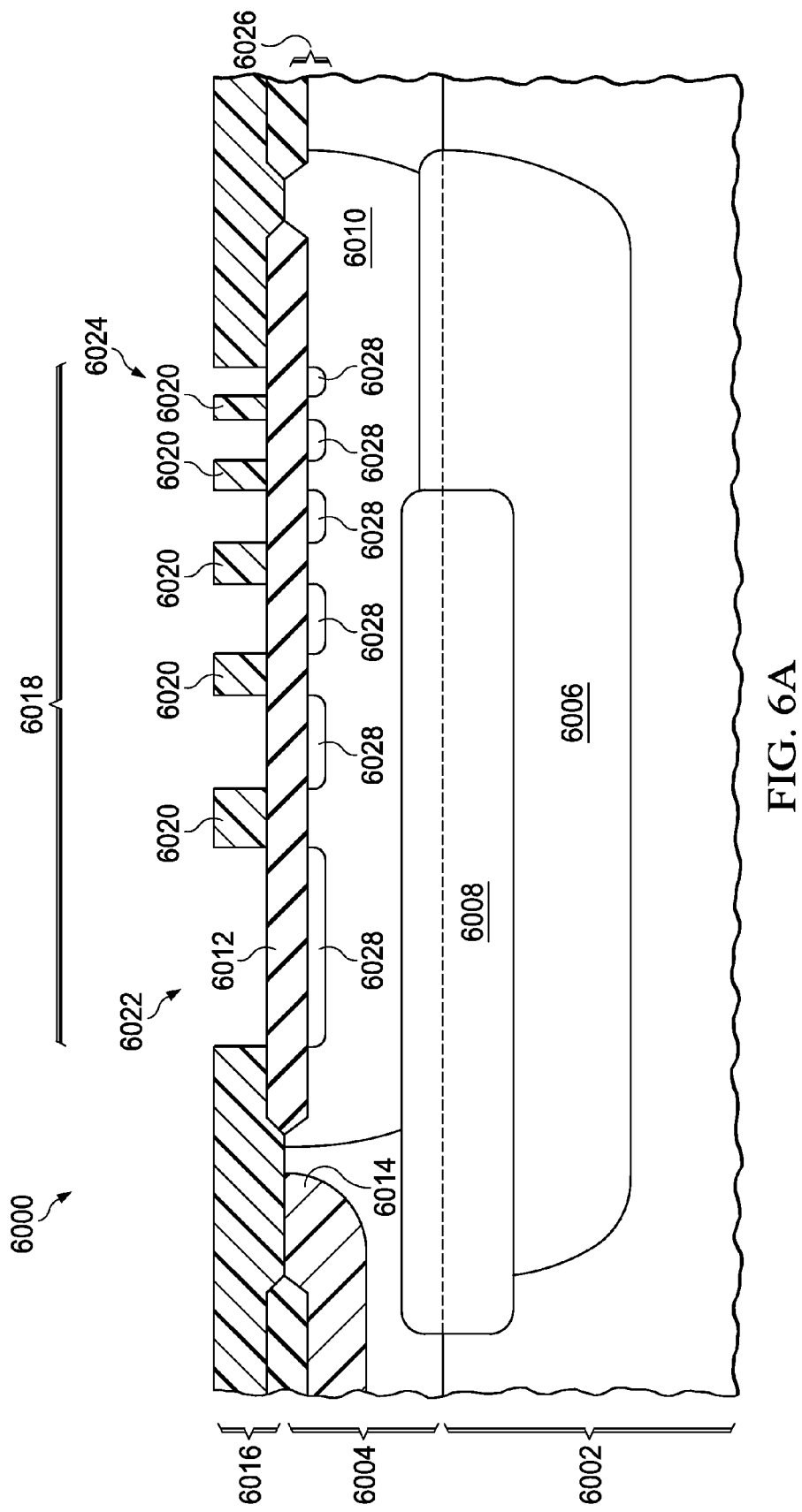
FIG. 6A and FIG. 6B are cross-sections of an integrated circuit including an extended drain MOS transistor with a graded upper RESURF layer, formed according to an example, depicted in successive stages of fabrication.
Figure 6B:
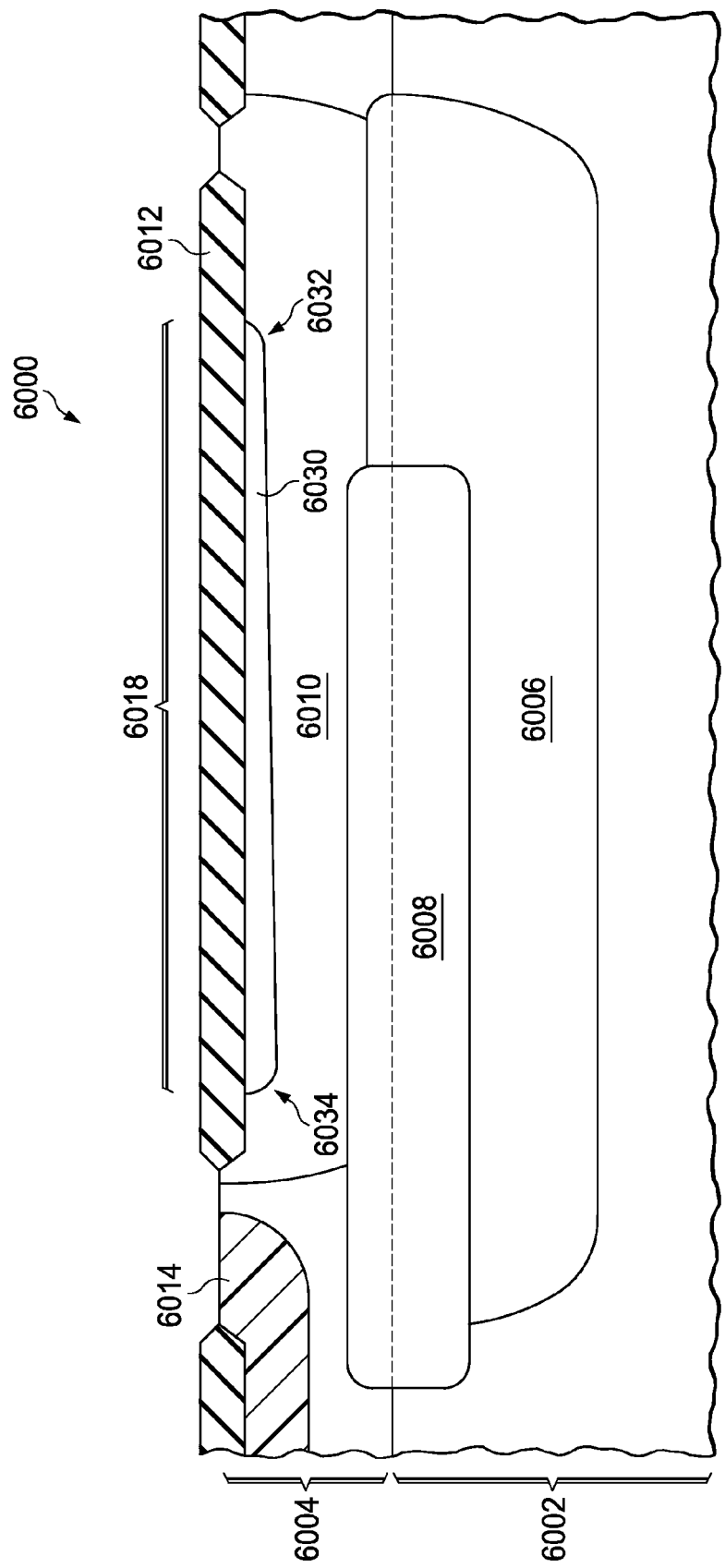

FIG. 6A and FIG. 6B are cross-sections of an integrated circuit including an extended drain MOS transistor with a graded upper RESURF layer, formed according to an example, depicted in successive stages of fabrication. Referring to FIG. 6A, the integrated circuit 6000 is formed in and on a substrate 6002 with the properties described in reference to FIG. 1. An epitaxial layer 6004 is formed on a top surface of the substrate 6002 as described in reference to FIG. 2A through FIG. 2C. A buried drain extension 6006 is formed in the substrate 6002 and epitaxial layer 6004 as described in reference to FIG. 2A through FIG. 2C, or possibly as described in reference to FIG. 3A and FIG. 3B. A lower RESURF layer 6008 is formed in the substrate 6002 and epitaxial layer 6004 as described in reference to FIG. 2B and FIG. 2C, or possibly as described in reference to FIG. 4A and FIG. 4B. A drift layer 6010 is formed in the epitaxial layer 6004 as described in reference to FIG. 2D, or possibly as described in reference to FIG. 5A and FIG. 5B. A dielectric layer 6012 is formed over a central portion of the drift layer as described in reference to FIG. 2E. A source well 6014 is formed in the epitaxial layer 6004 adjacent to a channel end of the drift layer 6010 as described in reference to FIG. 2E.

An upper RESURF implant mask 6016 is formed over an existing top surface of the integrated circuit 6000 so as to expose the top surface of the integrated circuit 6000 in an area defined for an upper RESURF layer 6018. The upper RESURF implant mask 6016 includes internal blocking elements 6020 with graded widths and/or spaced on graded intervals so that a larger portion of the top surface of the integrated circuit 6000 is exposed in a channel end area 6022 than in a drain end area 6024. The blocking elements 6020 may have substantially equal lateral dimensions or may have substantially different lateral dimensions. The upper RESURF implant mask 6016 may include photoresist and/or inorganic dielectric material such as silicon dioxide or silicon nitride. An upper RESURF implant process is performed on the integrated circuit 6000 which implants dopants into the epitaxial layer 6004 at a dose between $2\times10^{11}$ atoms/cm$^2$ and $1\times10^{13}$ atoms/cm$^2$ to form an upper RESURF segmented implanted layer 6026 in the epitaxial layer 6004. The upper RESURF segmented implanted layer 6026 includes implanted segments 6028 which may have different lateral dimensions.

Referring to FIG. 6B, an anneal operation is performed on the integrated circuit 6000 as described in reference to FIG. 2F. Dopants in the upper RESURF segmented implanted layer 6026 of FIG. 6A diffuse outward to form a graded upper RESURF layer 6030. A bottom surface of the graded upper RESURF layer 6030 contacts a top surface of the drift layer 6010. Forming the upper RESURF implant mask 6016 with internal blocking elements 6020 as described in reference to FIG. 6A results in the graded upper RESURF layer 6030 having a lower doping density at a drain end 6032 than at a channel end 6034. In one version of the instant example, a local average doping density of the graded upper RESURF layer 6030 at the channel end 6034 may be between $1\times10^{16}$ cm$^{-3}$ and $5\times10^{17}$ cm$^{-3}$, while a local average doping density of the graded upper RESURF layer 6030 at the drain end 6032 may be between 5 and 20 times lower.

Figure 7:
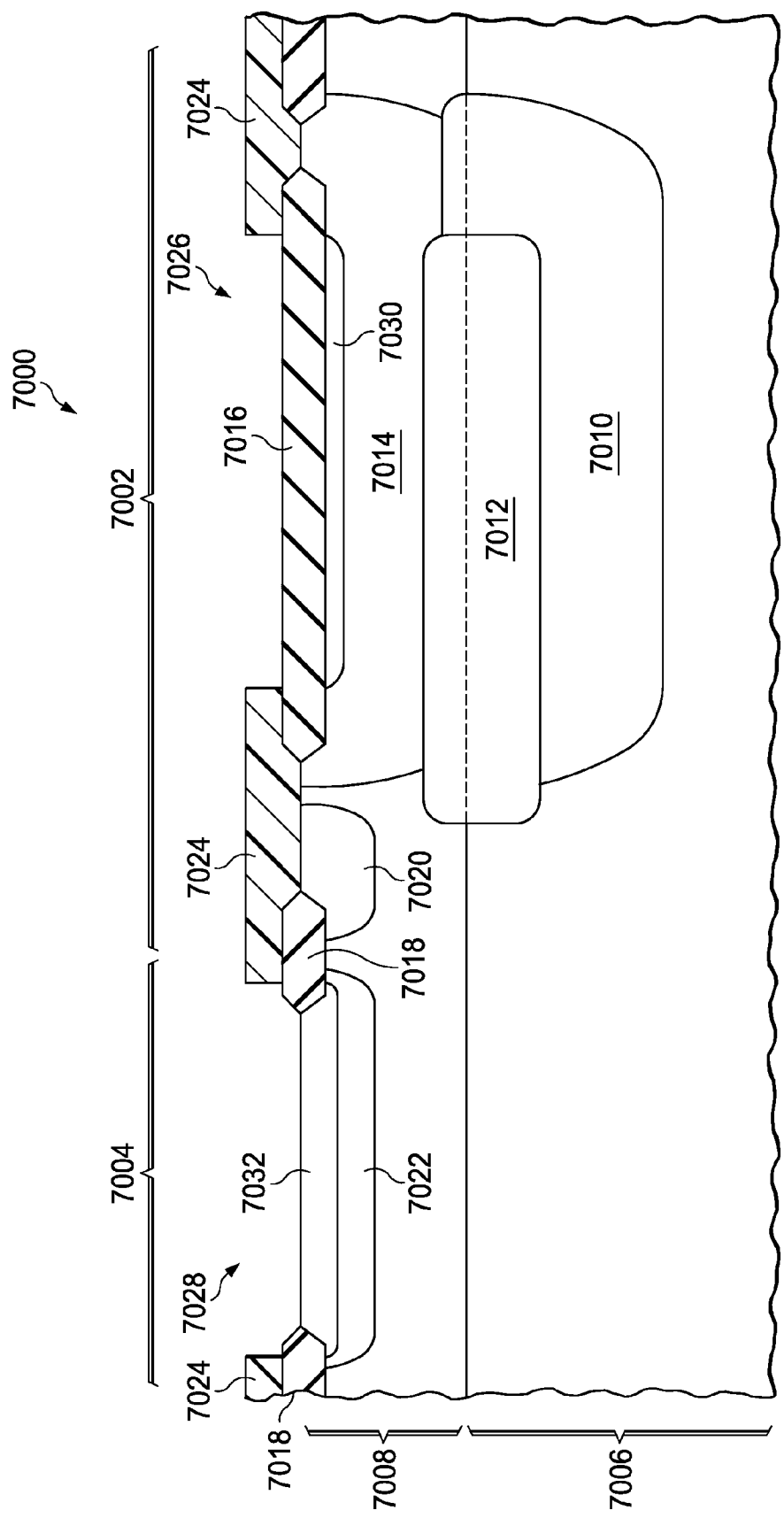
FIG. 7 is a cross-section of an integrated circuit containing an extended drain MOS transistor and a low voltage MOS transistor of a same polarity as the extended drain MOS transistor, formed according to an example.

FIG. 7 is a cross-section of an integrated circuit containing an extended drain MOS transistor and a low voltage MOS transistor of a same polarity as the extended drain MOS transistor, formed according to an example. The integrated circuit 7000 includes an area defined for the extended drain MOS transistor 7002 and an area defined for the low voltage MOS transistor 7004. The integrated circuit 7000 is formed in and on a substrate 7006 with the properties described in reference to FIG. 1. An epitaxial layer 7008 is formed on a top surface of the substrate 7006 as described in reference to FIG. 2A through FIG. 2C. A buried drain extension 7010 is formed in the substrate 7006 and epitaxial layer 7008 in the extended drain MOS transistor area 7002 as described in reference to FIG. 2A through FIG. 2C, or possibly as described in reference to FIG. 3A and FIG. 3B. A lower RESURF layer 7012 is formed in the substrate 7006 and epitaxial layer 7008 in the extended drain MOS transistor area 7002 as described in reference to FIG. 2B and FIG. 2C, or possibly as described in reference to FIG. 4A and FIG. 4B. A drift layer 7014 is formed in the epitaxial layer 7008 in the extended drain MOS transistor area 7002 as described in reference to FIG. 2D, or possibly as described in reference to FIG. 5A and FIG. 5B. A dielectric layer 7016 is formed over a central portion of the drift layer as described in reference to FIG. 2E. Additional elements of the dielectric layer 7018 may be formed to isolate the low voltage MOS transistor area 7004. A backgate well 7020 is formed in the epitaxial layer 7008 in the extended drain MOS transistor area 7002 adjacent to a channel end of the drift layer 7014 as described in reference to FIG. 2E. A backgate well 7022 may be formed in the low voltage MOS transistor area 7004 concurrently with the backgate well 7020.

An implant mask 7024 is formed over the integrated circuit 7000 which exposes an area for an upper RESURF implanted layer 7026 in the extended drain MOS transistor area 7002 and exposes an area for a channel stop implanted layer 7028 in the low voltage MOS transistor area 7004. An ion implant operation is performed on the integrated circuit 7000 which concurrently forms an upper RESURF implanted layer 7030 in the extended drain MOS transistor area 7002 and a channel stop implanted layer 7032 in the low voltage MOS transistor area 7004. A subsequent anneal operations causes dopants in the upper RESURF implanted layer 7030 and the channel stop implanted layer 7032 to diffuse and be activated to form an upper RESURF layer and a channel stop layer, respectively. Forming the upper RESURF implanted layer 7030 and the channel stop implanted layer 7032 concurrently may advantageously reduce fabrication costs of the integrated circuit 7000.

Figure 8:
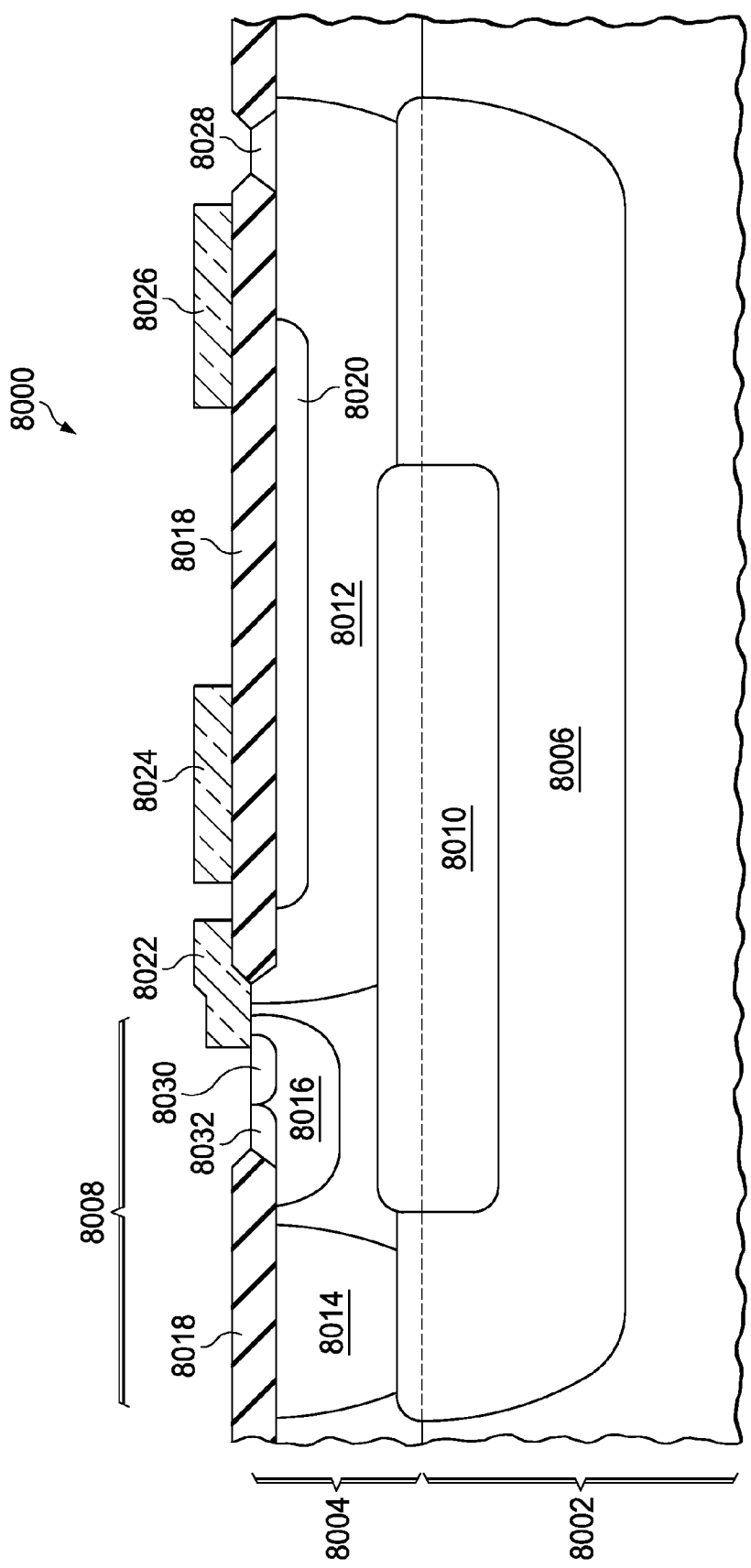
FIG. 8 is a cross-section of an integrated circuit containing an extended drain MOS transistor with an isolated source, formed according to an example.

FIG. 8 is a cross-section of an integrated circuit containing an extended drain MOS transistor with an isolated source, formed according to an example. The integrated circuit 8000 is formed in and on a substrate 8002 with the properties described in reference to FIG. 1. An epitaxial layer 8004 is formed on a top surface of the substrate 8002 as described in reference to FIG. 2A through FIG. 2C. A buried drain extension 8006 is formed in the substrate 8002 and epitaxial layer 8004 as described in reference to FIG. 2A through FIG. 2C, or possibly as described in reference to FIG. 3A and FIG. 3B, and such that the buried drain extension 8006 is electrically contiguous and extends below a source region 8008 of the MOS transistor. An optional lower RESURF layer 8010 may be formed in the substrate 8002 and epitaxial layer 8004 as described in reference to FIG. 2B and FIG. 2C, or possibly as described in reference to FIG. 4A and FIG. 4B.

A drift layer 8012 is formed in the epitaxial layer 8004 as described in reference to FIG. 2D, or possibly as described in reference to FIG. 5A and FIG. 5B. An isolating extension 8014 of the drift layer 8012 is formed in the epitaxial layer 8004 contacting the buried drain extension 8006 and laterally surrounding a backgate well 8016 of the MOS transistor so as to electrically isolate the backgate well 8016. The isolating extension 8014 abuts the drift layer 8012 at locations out of the plane of FIG. 8.

A dielectric layer 8018 is formed over a central portion of the drift layer 8012 and possibly over the isolating extension 8014. An upper RESURF layer 8020 is formed in the epitaxial layer 8004 so that a bottom surface of the upper RESURF layer 8020 contacts the drift layer 8012 as described in reference to FIG. 2F or possibly as described in reference to FIG. 6A and FIG. 6B. A gate 8022, a channel side field plate 8024 and a drain side field plate 8026 are formed on the epitaxial layer 8004 and dielectric layer 8018 as described in reference to FIG. 1. A drain diffused contact region 8028 is formed in the drift layer 8012 as described in reference to FIG. 1. A source 8030 and a body diffused contact region 8032 are formed in the isolated backgate well 8016. Forming the isolating extension 8014 so as to electrically isolate the backgate well 8016 may advantageously allow operating the MOS transistor with the source 8030 above a potential of the substrate 8002.

Figure 9:
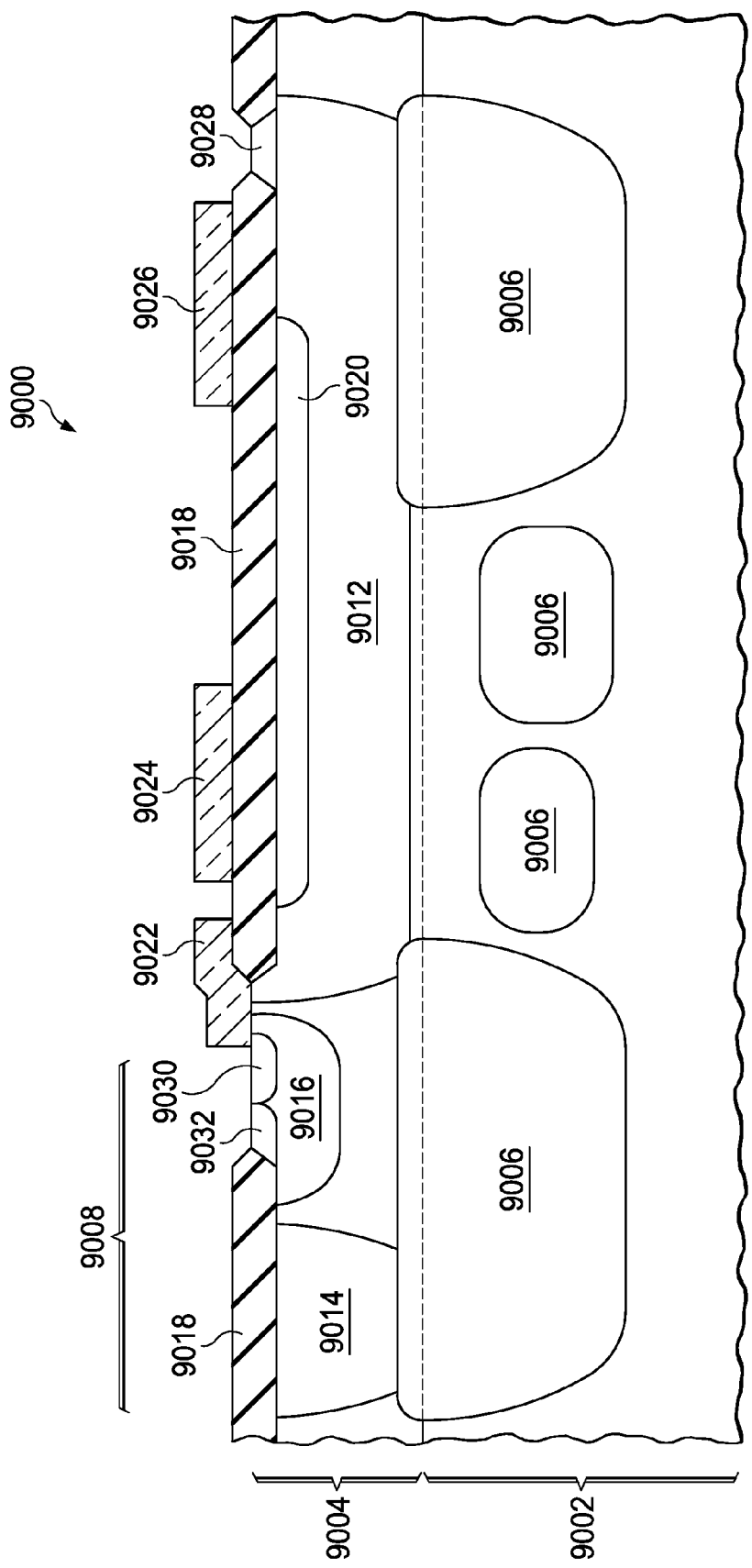
FIG. 9 is a cross-section of an integrated circuit containing an extended drain MOS transistor with an isolated source, formed according to an alternate example.

FIG. 9 is a cross-section of an integrated circuit containing an extended drain MOS transistor with an isolated source, formed according to an alternate example. The integrated circuit 9000 is formed in and on a substrate 9002 with the properties described in reference to FIG. 1. An epitaxial layer 9004 is formed on a top surface of the substrate 9002 as described in reference to FIG. 2A through FIG. 2C. A buried drain extension 9006 is formed in the substrate 9002 and epitaxial layer 9004 as described in reference to FIG. 3A and FIG. 3B, and such that the buried drain extension 9006 extends below a source region 9008 of the MOS transistor. The buried drain extension 9006 contains separated sections and is electrically discontinuous when a drain of the MOS transistor is not biased. An optional lower RESURF layer, not shown, may be formed in the substrate 9002 and epitaxial layer 9004 as described in reference to FIG. 2B and FIG. 2C, or possibly as described in reference to FIG. 4A and FIG. 4B.

A drift layer 9012 is formed in the epitaxial layer 9004 as described in reference to FIG. 2D, or possibly as described in reference to FIG. 5A and FIG. 5B. An isolating extension 9014 of the drift layer 9012 is formed in the epitaxial layer 9004 contacting the buried drain extension 9006 and laterally surrounding a backgate well 9016 of the MOS transistor so as to electrically isolate the backgate well 9016. The isolating extension 9014 abuts the drift layer 9012 at locations out of the plane of FIG. 8.

A dielectric layer 9018 is formed over a central portion of the drift layer 9012 and possibly over the isolating extension 9014. An upper RESURF layer 9020 is formed in the epitaxial layer 9004 so that a bottom surface of the upper RESURF layer 9020 contacts the drift layer 9012 as described in reference to FIG. 2F or possibly as described in reference to FIG. 6A and FIG. 6B. A gate 9022, a channel side field plate 9024 and a drain side field plate 9026 are formed on the epitaxial layer 9004 and dielectric layer 9018 as described in reference to FIG. 1. A drain diffused contact region 9028 is formed in the drift layer 9012 as described in reference to FIG. 1. A source 9030 and a body diffused contact region 9032 are formed in the isolated backgate well 9016. During operation of the MOS transistor, biasing the drain diffused contact region 9028 causes the buried drain extension 9006 to be continuously depleted and thereby to isolate the backgate well 9016. Forming the isolating extension 9014 so as to electrically isolate the backgate well 9016 and forming the buried drain extension 9006 in a discontinuous configuration may advantageously allow operating the MOS transistor with the source 9030 above a potential of the substrate 9002 while providing a higher voltage operating capability than other configurations of MOS transistors with a similar size.

Figure 10A:
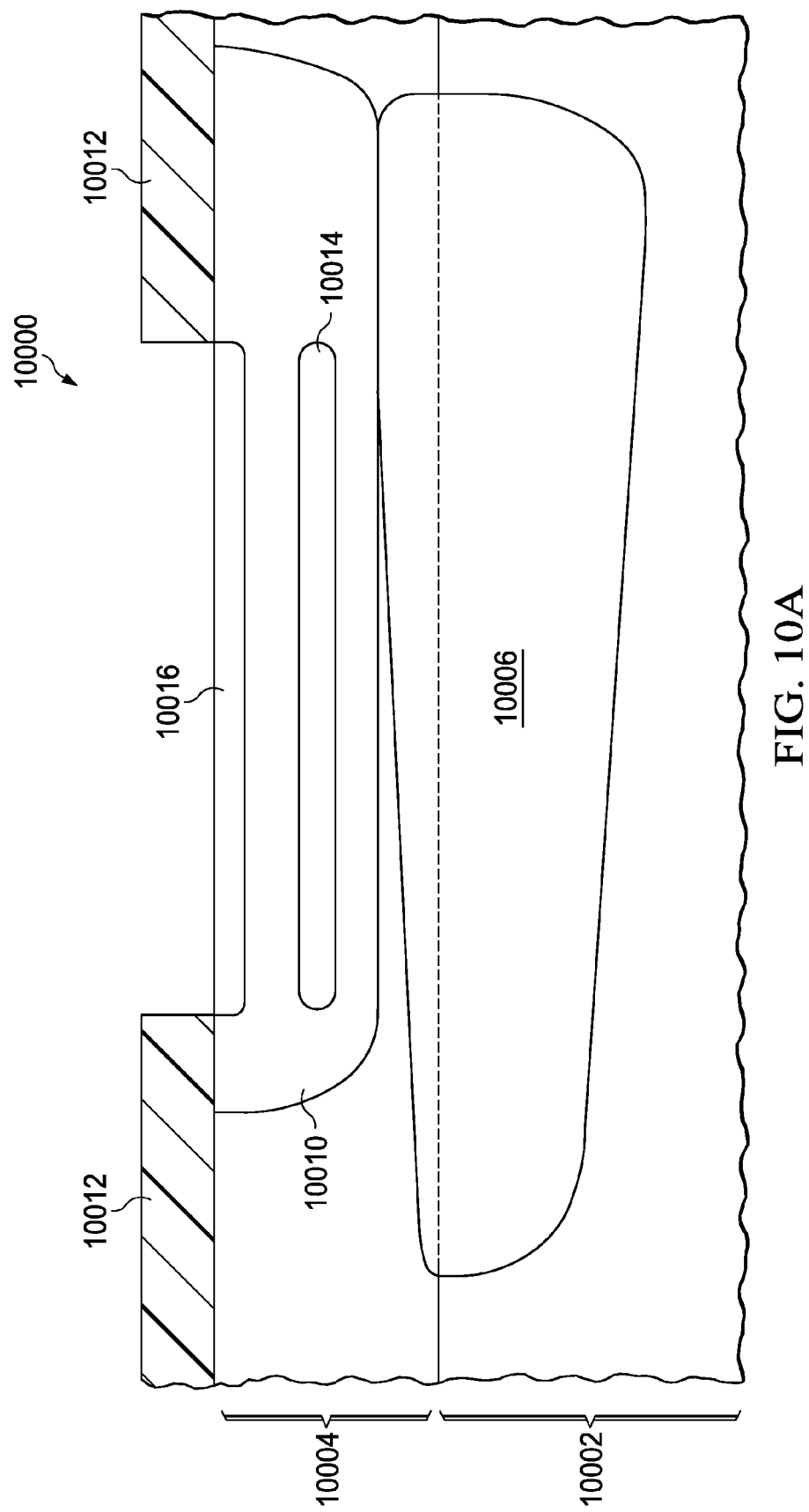
FIG. 10A and FIG. 10B are cross-sections of an integrated circuit containing an extended drain MOS transistor which includes an immersed RESURF layer in a drift layer, formed according to an example, depicted in successive stages of fabrication.
Figure 10B:
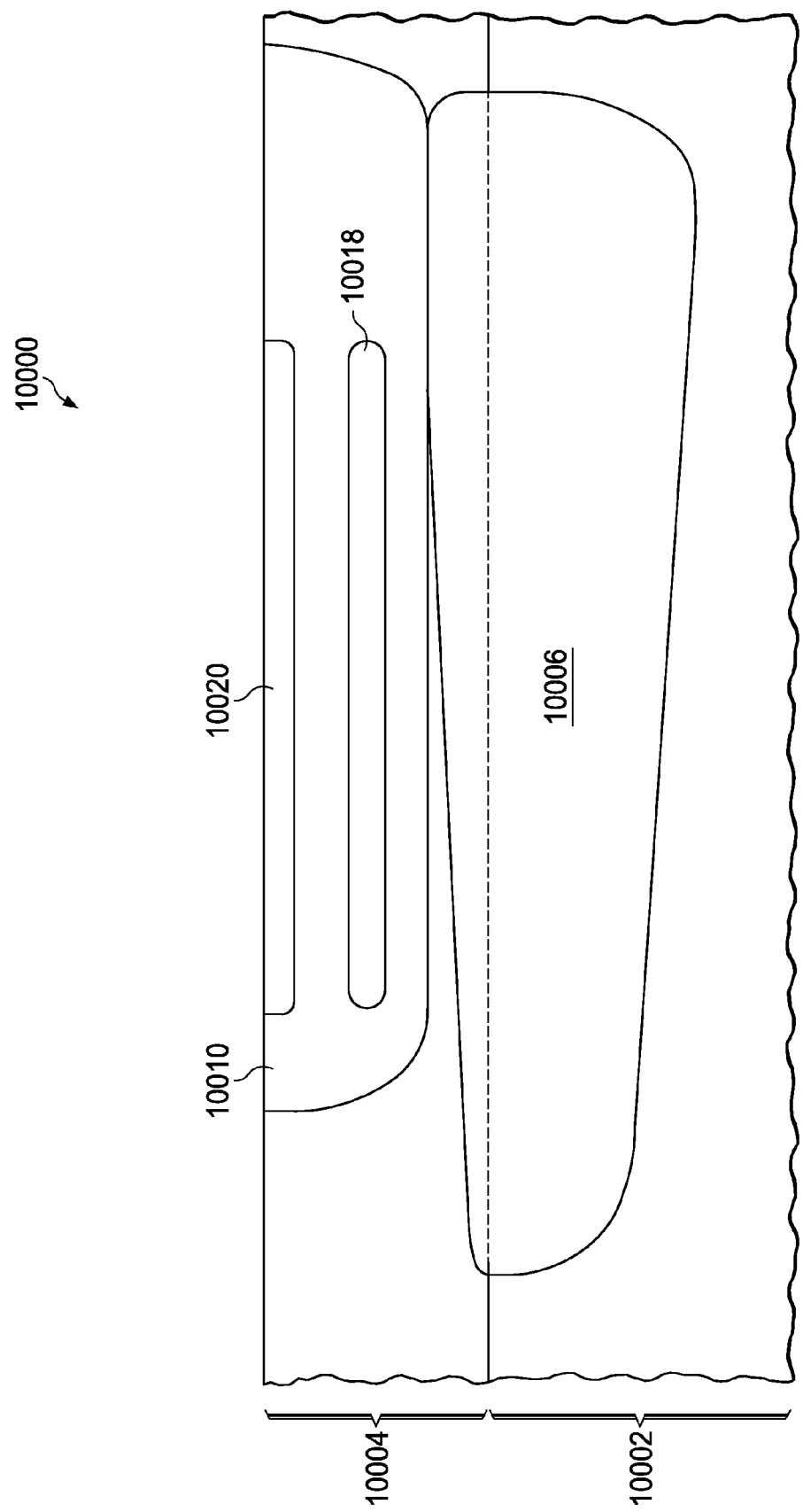

FIG. 10A and FIG. 10B are cross-sections of an integrated circuit containing an extended drain MOS transistor which includes an immersed RESURF layer in a drift layer, formed according to an example, depicted in successive stages of fabrication. Referring to FIG. 10A, the integrated circuit 10000 is formed in and on a substrate 10002 with the properties described in reference to FIG. 1. An epitaxial layer 10004 is formed on a top surface of the substrate 10002 as described in reference to FIG. 2A through FIG. 2C. A buried drain extension 10006 is formed in the substrate 10002 and epitaxial layer 10004 as described in reference to FIG. 2A through FIG. 2C, or possibly as described in reference to FIG. 3A and FIG. 3B as depicted in FIG. 10A. An optional lower RESURF layer, not shown, is formed in the substrate 10002 and epitaxial layer 10004 as described in reference to FIG. 2B and FIG. 2C, or possibly as described in reference to FIG. 4A and FIG. 4B. A drift layer 10010 is formed in the epitaxial layer 10004 as described in reference to FIG. 2D, or possibly as described in reference to FIG. 5A.

An immersed RESURF implant mask 10012 is formed over an existing top surface of the integrated circuit 10000 so as to expose an area defined for an immersed RESURF layer. An immersed RESURF ion implant operation is performed on the integrated circuit 10000 which implants dopants into the drift layer 10010 in the immersed RESURF layer area to form an immersed RESURF implanted layer 10014. The dopants used in the immersed RESURF ion implant operation are of an opposite conductivity type from dopants in the drift layer 10010. Optionally, an upper RESURF ion implant operation may be performed on the integrated circuit 10000 which implants dopants into the drift layer 10010 in the immersed RESURF layer area to form an optional upper RESURF implanted layer 10016 at or proximate to a top surface of the epitaxial layer 10004. The dopants used in the upper RESURF ion implant operation are of an opposite conductivity type from dopants in the drift layer 10010.

Referring to FIG. 10B, an anneal operation is performed on the integrated circuit 10000 which activates the dopants in the immersed RESURF implanted layer 10014 of FIG. 10A to form an immersed RESURF layer 10018 at a depth between one third and two thirds of a depth of the drift layer 10010, so that the drift layer 10010 extends above and below the immersed RESURF layer 10018. The anneal operation also activates dopants in the upper RESURF implanted layer 10016 if present to form an upper RESURF layer 10020 at the top surface of the epitaxial layer 10004. The immersed RESURF layer 10018 and the upper RESURF layer 10020 have an opposite conductivity type from the drift layer 10010. Forming the immersed RESURF layer 10018 in the drift layer 10010 may advantageously improve an on-state current density of the MOS transistor at a desired operating voltage. Forming the upper RESURF layer 10020 using the immersed RESURF implant mask 10012 may advantageously reduce fabrication costs of the integrated circuit 10000.

Figure 11A:
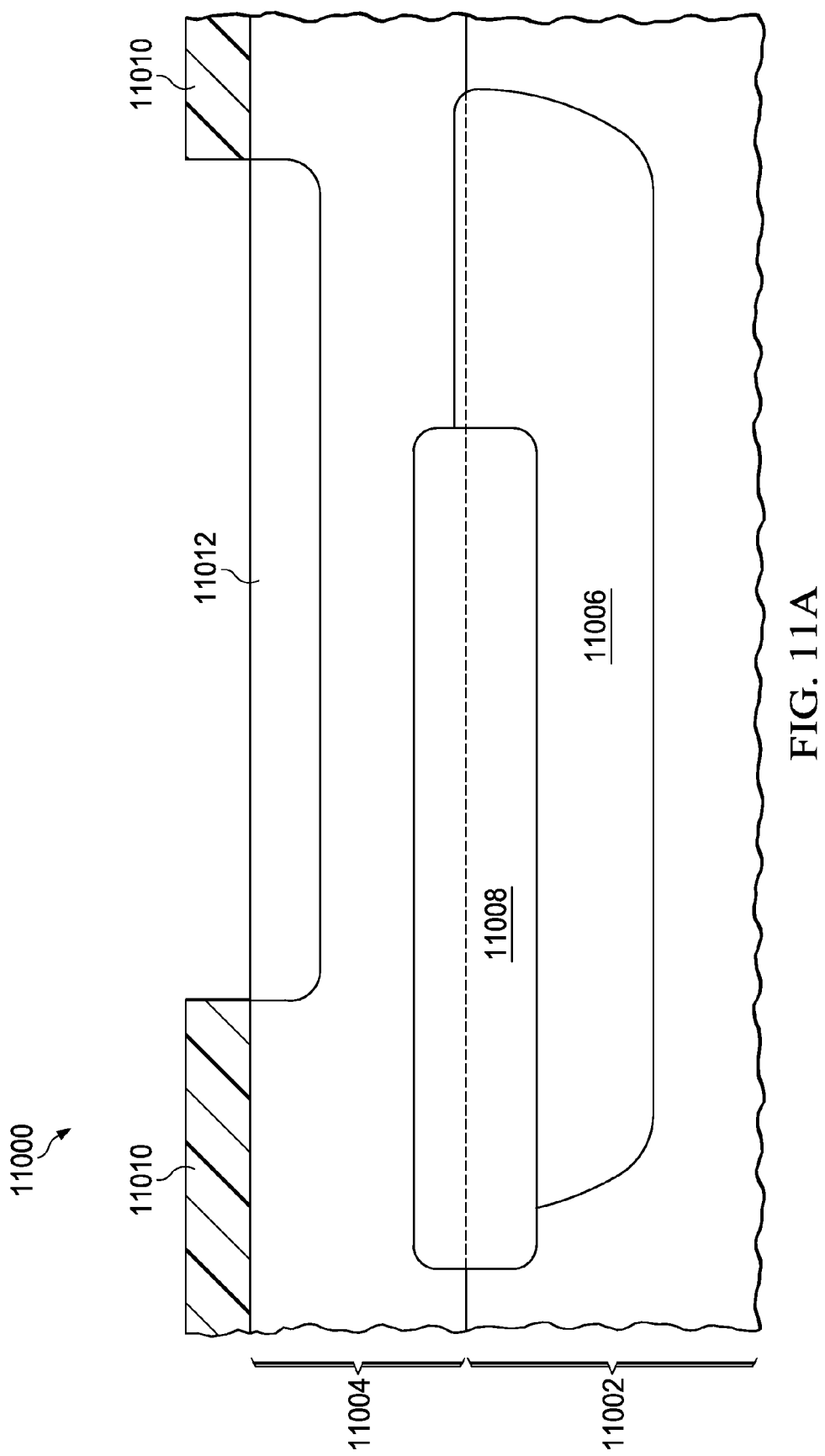
FIG. 11A through FIG. 11C are cross sections of an integrated circuit containing an extended drain MOS transistor formed according to an example, depicted in successive stages of fabrication.
Figure 11B:
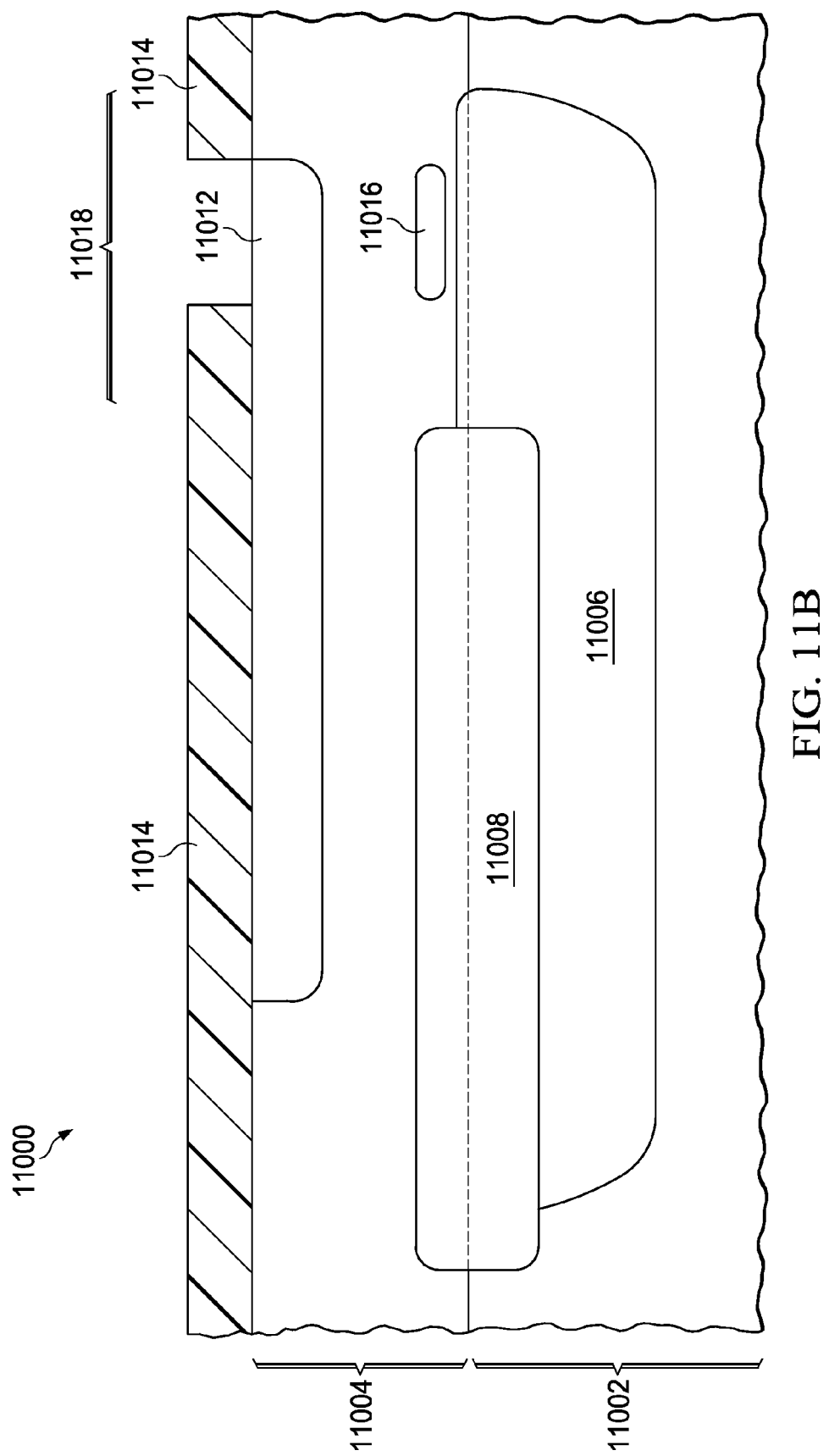
Figure 11C:
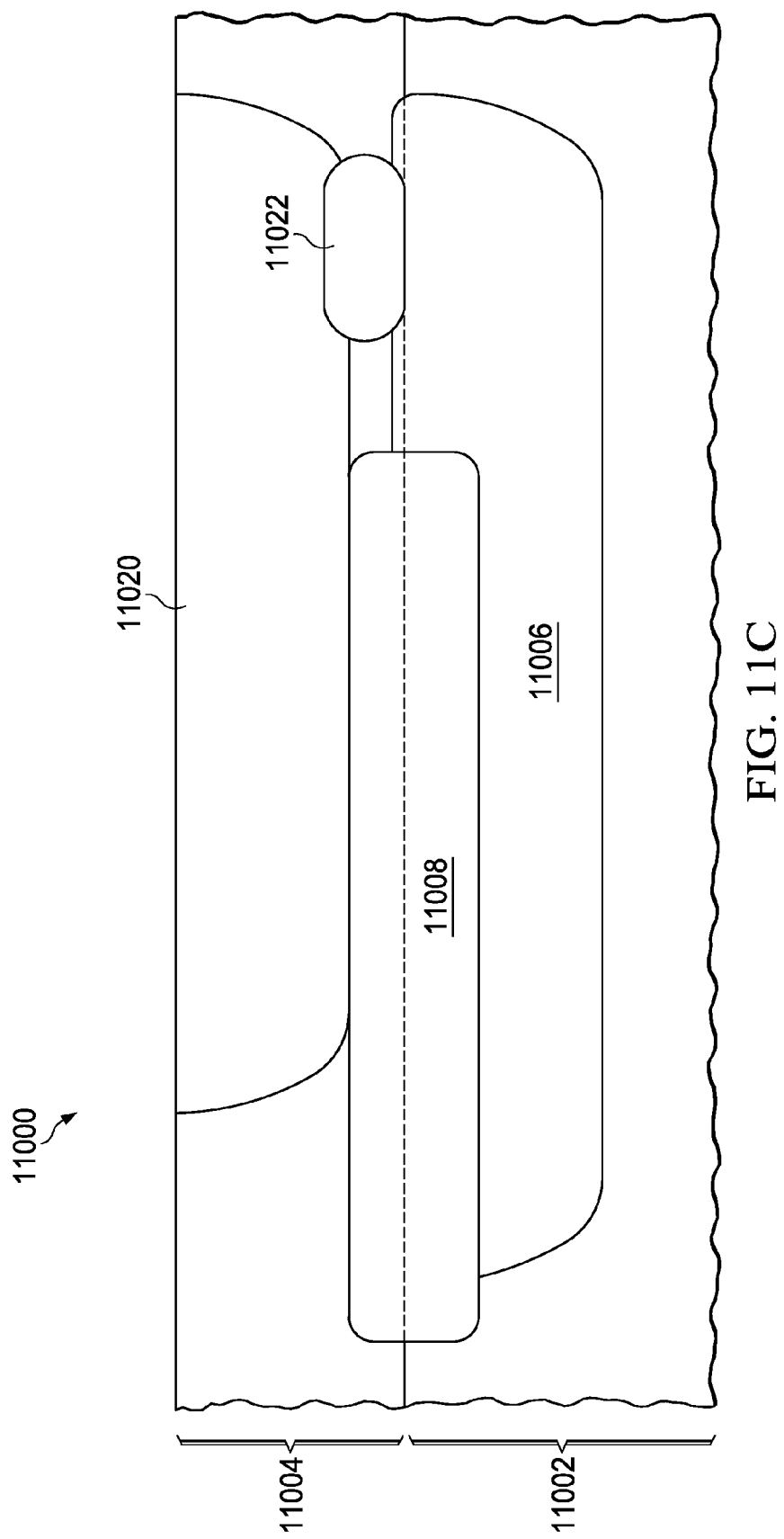

FIG. 11A through FIG. 11C are cross sections of an integrated circuit containing an extended drain MOS transistor formed according to an example, depicted in successive stages of fabrication. Referring to FIG. 11A, the integrated circuit 11000 is formed in and on a substrate 11002 with the properties described in reference to FIG. 1. An epitaxial layer 11004 is formed on a top surface of the substrate 11002 as described in reference to FIG. 2A through FIG. 2C. A buried drain extension 11006 is formed in the substrate 11002 and epitaxial layer 11004 as described in reference to FIG. 2A through FIG. 2C, or possibly as described in reference to FIG. 3A and FIG. 3B. An optional lower RESURF layer 11008 may be formed in the substrate 11002 and epitaxial layer 11004 as described in reference to FIG. 2B and FIG. 2C, or possibly as described in reference to FIG. 4A and FIG. 4B. A drift layer implant mask 11010 is formed over a top surface of the epitaxial layer 11004 so as to expose the top surface of the epitaxial layer 11004 in an area defined for a drift layer. A drift layer implant process is performed on the integrated circuit 11000 which implants dopants into the epitaxial layer 11004 at a dose between $2 \times 10^{11}$ atoms/cm$^2$ and $3 \times 10^{12}$ atoms/cm$^2$ to form a drift implanted layer 11012 in the epitaxial layer 11004.

Referring to FIG. 11B, a drain link implant mask 11014 is formed over the top surface of the epitaxial layer 11004 so as to expose the top surface of the epitaxial layer 11004 in an area defined for a drain link. A drain link implant process is performed on the integrated circuit 11000 which implants dopants into the epitaxial layer 11004 at a dose between $2 \times 10^{11}$ atoms/cm$^2$ and $3 \times 10^{12}$ atoms/cm$^2$ to form a drain link implanted layer 11016 in the epitaxial layer 11004 between the drift implanted layer 11012 and the buried drain extension 11006 in a drain area 11018 of the MOS transistor.

Referring to FIG. 11C, a thermal drive operation is performed which causes dopants in the drift implanted layer 11012 and the drain link implanted layer 11016 to diffuse outward and form a drift layer 11020 and a drain link 11022 respectively. The drain link 11022 overlaps the drift layer 11020 and the buried drain extension 11006 so that the drift layer 11020 and the buried drain extension 11006 are electrically connected through the drain link 11022.

FIG. 12 through FIG. 16 are top views of integrated circuits containing extended drain MOS transistors formed according to examples, depicting various implant masks for graded layers as discussed in reference to FIG. 3A and FIG. 3B, FIG. 4A and FIG. 4B, FIG. 5A and FIG. 5B, and FIG. 6A and FIG.

Figure 12:
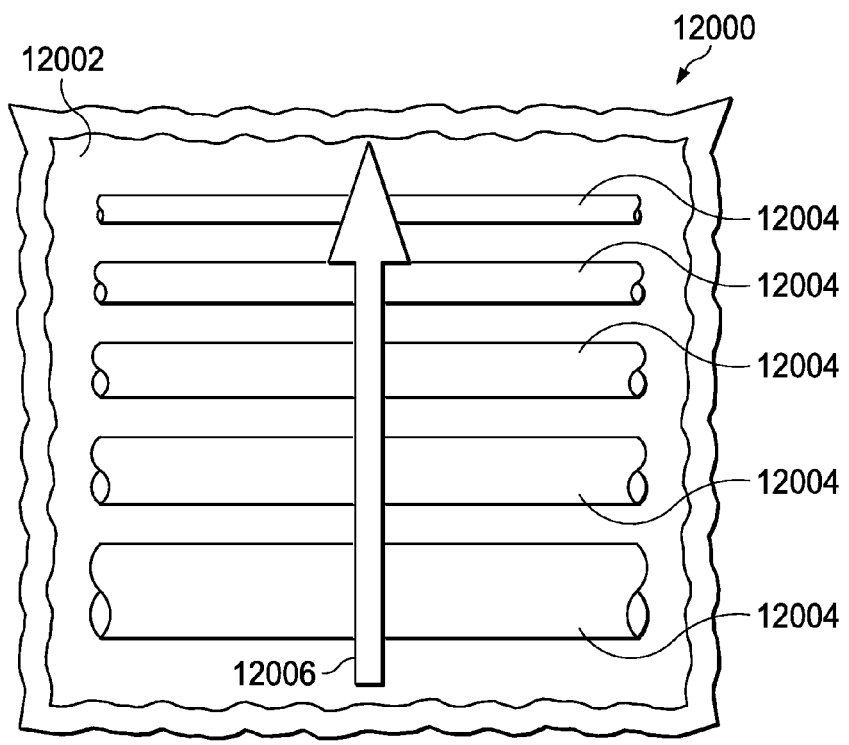
FIG. 12 through FIG. 16 are top views of integrated circuits containing extended drain MOS transistors formed according to examples, depicting various implant masks for graded layers.

6B. Referring to FIG. 12, the integrated circuit 12000 has an implant mask 12002 on it for a graded layer which has exposed areas 12004 which of decreasing widths. In the instant example, the exposed areas 12004 are linear and oriented perpendicular to a direction of current flow in the MOS transistor, as indicated by current flow arrow 12006.

Figure 13:
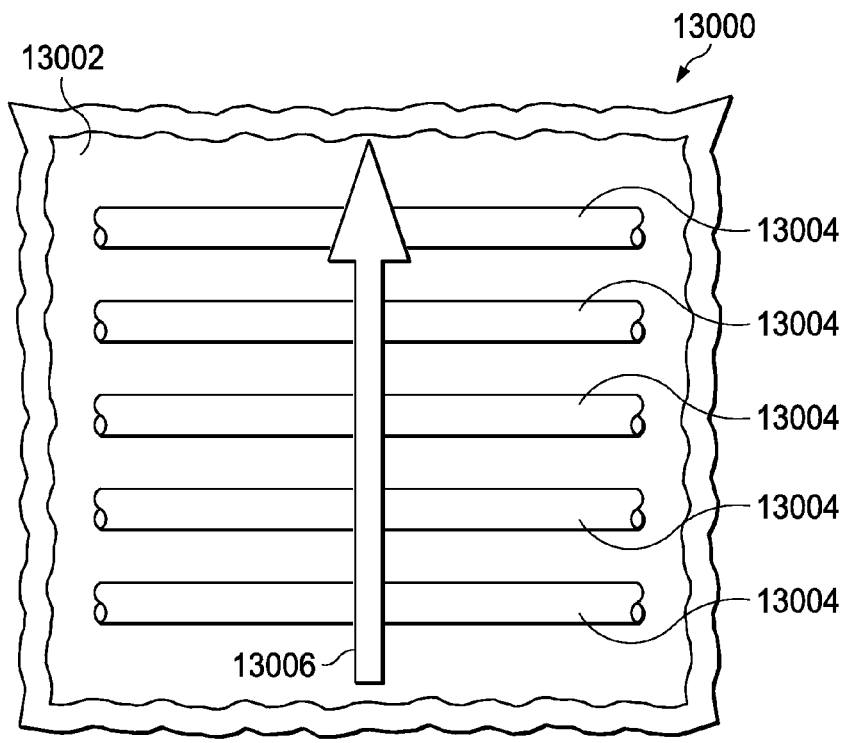

Referring to FIG. 13, the integrated circuit 13000 has an implant mask 13002 on it for a graded layer which has exposed areas 13004 which are spaced at substantially equal intervals. In the instant example, the exposed areas 13004 are linear and oriented perpendicular to a direction of current flow in the MOS transistor, as indicated by current flow arrow 13006.

Figure 14:
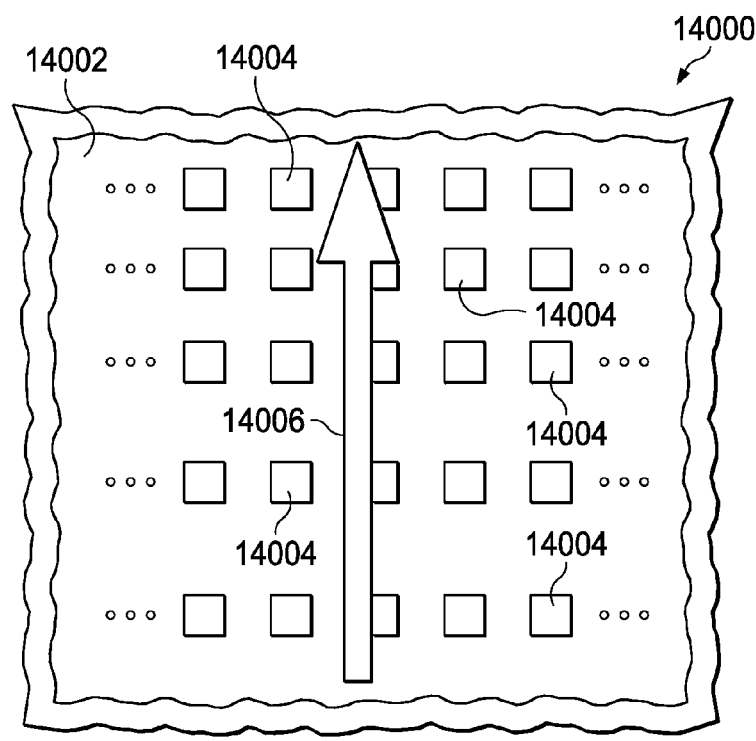

Referring to FIG. 14, the integrated circuit 14000 has an implant mask 14002 on it for a graded layer which has exposed areas 14004 which are spaced at increasing intervals. In the instant example, the exposed areas 14004 are discrete segments of substantially equal size. The increasing spacing intervals are oriented perpendicular to a direction of current flow in the MOS transistor, as indicated by current flow arrow 14006.

Figure 15:
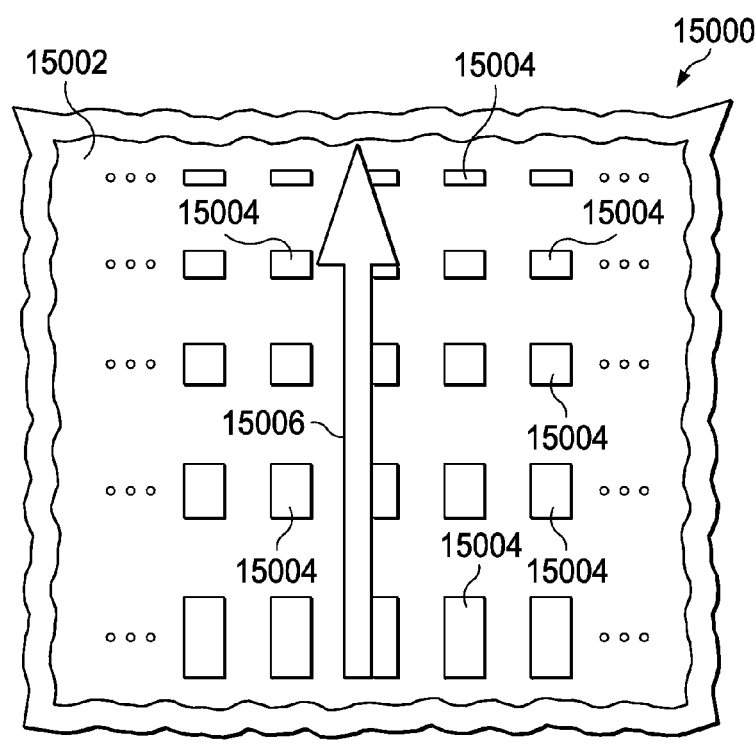

Referring to FIG. 15, the integrated circuit 15000 has an implant mask 15002 on it for a graded layer which has exposed areas 15004 which are spaced at increasing intervals. In the instant example, the exposed areas 15004 are discrete segments of decreasing size. The direction of decreasing size is oriented parallel to a direction of current flow in the MOS transistor, as indicated by current flow arrow 15006.

Figure 16:
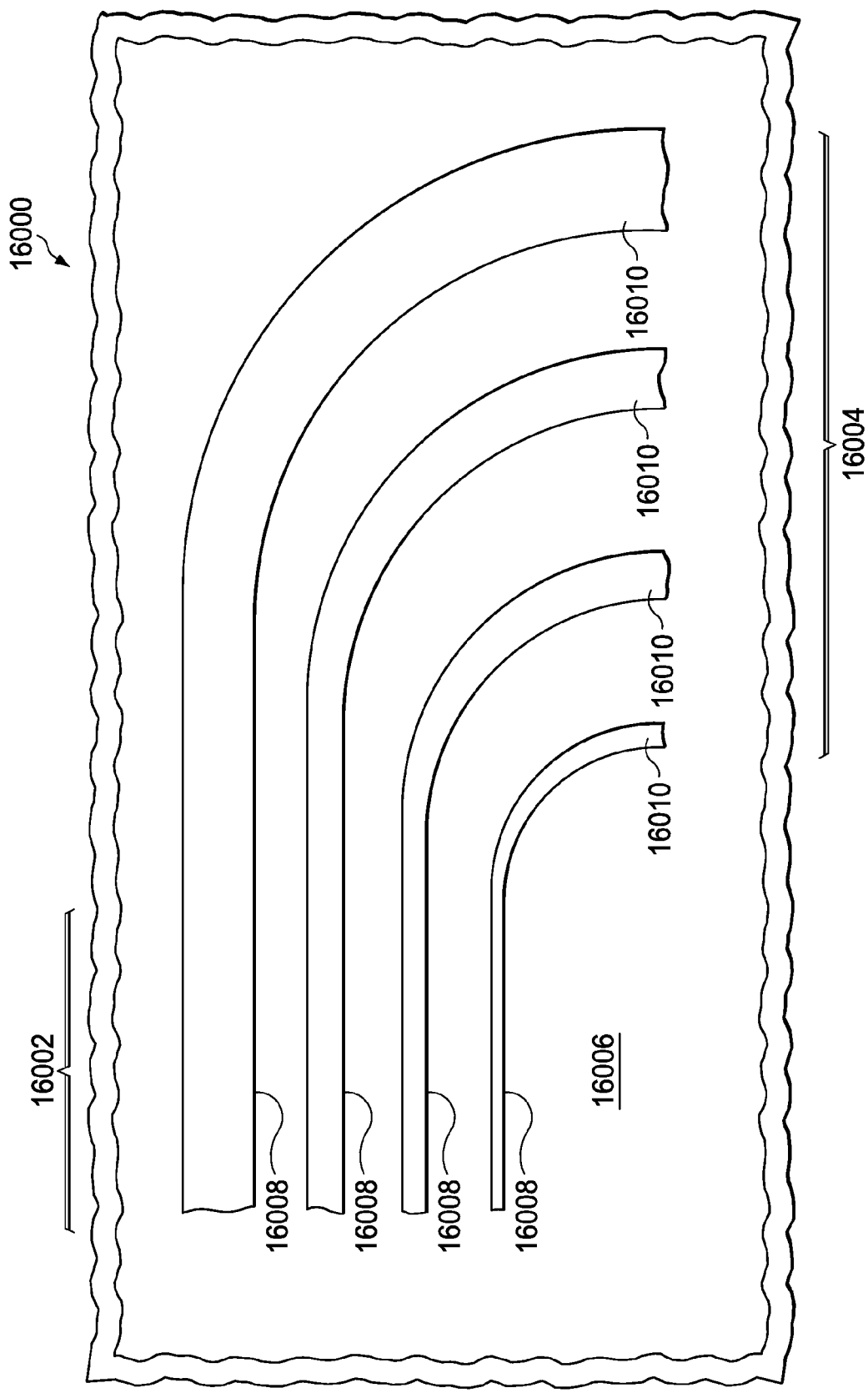

Referring to FIG. 16, the integrated circuit 16000 contains an extended drain MOS transistor formed according to an example. The MOS transistor includes a linear portion 16002 and a rounded portion 16004, as may be found in a racetrack configuration or a finger configuration, for example. The integrated circuit has an implant mask 16006 on it for a graded layer. In the linear portion 16002, the implant mask 16006 has linear exposed areas 16008. In the rounded portion 16004, the implant mask 16006 has rounded exposed areas 16010. Widths and spacings of the linear exposed areas 16008 are not equal to corresponding widths and spacings of the rounded exposed areas 16010. Forming the rounded exposed areas 16012 with different widths and spacings from the linear exposed areas 16008 may advantageously improve a uniformity of current density in the MOS transistor.

While various examples of the present invention have been described above, it should be understood that they have been presented by way of example only and not limitation. Numerous changes to the disclosed examples can be made in accordance with the disclosure herein without departing from the spirit or scope of the invention. Thus, the breadth and scope of the present invention should not be limited by any of the above described examples. Rather, the scope of the invention should be defined in accordance with the following claims and their equivalents.

What is claimed is:

1. An integrated circuit, comprising:
   a semiconductor substrate having a first conductivity type;
   an epitaxial layer disposed on a top surface of the semiconductor substrate, the epitaxial layer having the first conductivity type; and
   an extended drain metal oxide semiconductor (MOS) transistor including:
      a drift layer formed in the epitaxial layer, the drift layer having a second conductivity type opposite of the first conductivity type, and the drift layer contacting a drain diffused contact region and proximate to a channel region of the extended drain MO S transistor;
      an upper RESURF layer formed in the epitaxial layer over the drift layer to contact a top surface of the drift layer spaced apart from a source diffused contact region, the upper RESURF layer having the first conductivity type; and
      a buried drain extension formed in the substrate, the buried drain extension abutting the drift layer below the drain diffused contact region and separated from the drift layer below the channel region, the buried drain extension having the second conductivity type.

2. The integrated circuit of claim 1, wherein a local average doping density of the upper RESURF layer proximate to the channel region is between $1 \times 10^{16}$ cm$^{-3}$ and $5 \times 10^{17}$ cm$^{-3}$, and a local average doping density of the upper RESURF layer proximate to the drain diffused contact region is between 5 and 20 times lower than the local average doping density of the upper RESURF layer proximate to the channel region.

3. The integrated circuit of claim 1, wherein a local average doping density of the drift layer proximate to the drain diffused contact region is between $5 \times 10^{15}$ cm$^{-3}$ and $5 \times 10^{16}$ cm$^{-3}$, and a local average doping density of the drift layer proximate to the channel region is between 5 and 20 times lower than the local average doping density of the drift layer proximate to the drain diffused contact region.

4. The integrated circuit of claim 1, wherein a local average doping density of the buried drain extension proximate to the drain diffused contact region is between $5 \times 10^{15}$ cm$^{-3}$ and $5 \times 10^{16}$ cm$^{-3}$, and a local average doping density of the buried drain extension proximate to the channel region is between 5 and 20 times lower than the local average doping density of the buried drain extension proximate to the drain diffused contact region.

5. The integrated circuit of claim 1, wherein the extended drain MOS transistor further includes a lower RESURF layer disposed between the drift layer and the buried drain extension, the lower RESURF layer having the first conductivity type.

6. The integrated circuit of claim 5, wherein a local average doping density of the lower RESURF layer proximate to the channel region is between $1 \times 10^{15}$ cm$^{-3}$ and $1 \times 10^{17}$ cm$^{-3}$, and a local average doping density of the lower RESURF layer proximate to the drain diffused contact region is between 5 and 20 times lower than the local average doping density of the lower RESURF layer proximate to the channel region.

7. The integrated circuit of claim 1, wherein:
   the buried drain extension is electrically contiguous and extends below a source region of the extended drain MOS transistor; and
   the drift layer includes an isolating extension contacting the buried drain extension and laterally surrounding a backgate well of the extended drain MOS transistor so as to electrically isolate the backgate well.

8. The integrated circuit of claim 1, further including a drain link between the drift layer and the buried drain extension proximate to the drain diffused contact region, the drain link having the second conductivity type, so that the drift layer is electrically connected to the buried drain extension through the drain link.

9. The integrated circuit of claim 1, wherein the extended drain MOS transistor further includes an immersed RESURF layer disposed in the drift layer at a depth between one third and two thirds of a depth of the drift layer so that the drift layer extends above and below the immersed RESURF layer, the immersed RESURF layer having the first conductivity type.

* * * * *